(12) United States Patent
Wang et al.

(10) Patent No.: US 10,881,461 B2
(45) Date of Patent: Jan. 5, 2021

(54) METHOD OF ANALYZING HOLLOW ANATOMICAL STRUCTURES FOR PERCUTANEOUS IMPLANTATION

(71) Applicant: Henry Ford Health System, Detroit, MI (US)

(72) Inventors: Dee Dee Wang, Ypsilanti, MI (US); William O'Neill, Grosse Pointe Farms, MI (US); Eric Myers, Ferndale, MI (US); Michael Forbes, Dearborn, MI (US)

(73) Assignee: Henry Ford Health System, Detroit, MI (US)

( * ) Notice: Subject to any disclaimer, the term of this patent is extended or adjusted under 35 U.S.C. 154(b) by 247 days.

(21) Appl. No.: 14/820,617

(22) Filed: Aug. 7, 2015

(65) Prior Publication Data
US 2016/0038246 A1 Feb. 11, 2016

Related U.S. Application Data

(60) Provisional application No. 62/034,251, filed on Aug. 7, 2014.

(51) Int. Cl.
*A61B 34/10* (2016.01)
*A61B 6/03* (2006.01)
(Continued)

(52) U.S. Cl.
CPC ............ *A61B 34/10* (2016.02); *A61B 6/032* (2013.01); *A61B 6/503* (2013.01); *A61B 6/504* (2013.01);
(Continued)

(58) Field of Classification Search
None
See application file for complete search history.

(56) References Cited

U.S. PATENT DOCUMENTS 8,494,245 B2   7/2013  Liao et al.
8,666,714 B2   3/2014  Whirley et al.
(Continued)

FOREIGN PATENT DOCUMENTS

WO    WO2013171039 A1    11/2013

OTHER PUBLICATIONS

Feuchtner, Gudrun. "Imaging of Cardiac Valves by Computed Tomography". Hindawi Publishing Corporation; Scientifica, vol. 2013, Article ID 270579, 13 pages.*

(Continued)

*Primary Examiner* — James M Kish
(74) *Attorney, Agent, or Firm* — Reising Ethington P.C.; Jeffrey L. Doyle

(57) ABSTRACT

A method of analyzing a hollow anatomical structure of interest for percutaneous implantation. The method comprises acquiring image data of an anatomical region of interest that includes the anatomical structure of interest, and generating a segmented model of the anatomical region of interest using the acquired image data. The method further comprises obtaining image(s) of the anatomical structure of interest by sectioning out intervening anatomical structures from the segmented model thereof, identifying one or more pertinent landmarks of the anatomical structure of interest in the acquired image(s), and measuring at least one of a circumference, a maximal diameter, or a minimal diameter of one or more features of the anatomical structure of interest contained in the acquired image(s) to determine an anatomical structure size. The method still further comprises reconciling the anatomical structure size and an implant size.

21 Claims, 37 Drawing Sheets

(51) Int. Cl.
  *A61B 6/00* (2006.01)
  *G06T 17/00* (2006.01)
  *G06T 7/73* (2017.01)
  *G06T 7/62* (2017.01)
  *A61B 5/107* (2006.01)

(52) U.S. Cl.
  CPC .............. *A61B 6/5217* (2013.01); *G06T 7/62* (2017.01); *G06T 7/73* (2017.01); *G06T 17/00* (2013.01); *A61B 5/1073* (2013.01); *A61B 5/1075* (2013.01); *A61B 6/463* (2013.01); *A61B 6/481* (2013.01); *A61B 6/5223* (2013.01); *A61B 6/5258* (2013.01); *A61B 2034/102* (2016.02); *A61B 2034/105* (2016.02); *A61B 2034/107* (2016.02); *A61B 2034/108* (2016.02); *A61B 2576/023* (2013.01); *G06T 2207/10081* (2013.01); *G06T 2207/30048* (2013.01)

(56) References Cited

U.S. PATENT DOCUMENTS

| | | | |
|---|---|---|---|
| 8,771,189 B2 | 7/2014 | Ionasec et al. | |
| 8,775,133 B2 | 7/2014 | Schroeder | |
| 2007/0293734 A1* | 12/2007 | Coste-Maniere | B25J 9/1671 600/300 |
| 2008/0123910 A1* | 5/2008 | Zhu | A61B 90/36 382/128 |
| 2010/0215213 A1* | 8/2010 | Mielekamp | A61B 17/3403 382/103 |
| 2010/0228534 A1* | 9/2010 | Gilboa | A61B 90/36 703/11 |
| 2010/0312096 A1* | 12/2010 | Guttman | A61B 34/10 600/411 |
| 2011/0153286 A1 | 6/2011 | Zaeuner et al. | |
| 2012/0232386 A1 | 9/2012 | Mansi et al. | |
| 2012/0323545 A1 | 12/2012 | Aulbach et al. | |
| 2013/0073025 A1 | 3/2013 | Kassab | |
| 2013/0129173 A1 | 5/2013 | Grbic et al. | |
| 2013/0230225 A1* | 9/2013 | Waechter-Stehle | A61B 6/463 382/131 |
| 2014/0120505 A1* | 5/2014 | Rios | G09B 23/285 434/219 |
| 2015/0119692 A1* | 4/2015 | McHenry | A61B 5/4851 600/411 |
| 2017/0084029 A1* | 3/2017 | Piazza | A61B 5/1075 |

OTHER PUBLICATIONS

Zhong et al., "Automatic Heart Isolation in 3D CT Images". B.H. Menze et al. (Eds.): MCV 2012, LNCS 7766, pp. 165-180, 2013.*
Torres et al., "A user-friendly automated port placement planning system for laparoscopic robotic surge". SPIE Medical Imaging, 2014, San Diego, California, United States; Mar. 12, 2014. 8 pages. (Year: 2014).*
Marescaux et al, "Augmented Reality and Minimally Invasive Surgery". Journal of GHR; May 21, 2013 2(5): pp. 555-560. (Year: 2013).*
Maslow, Andrew D., et al.; Echocardiographic Predictors of Left Ventricular Outflow Tract Obstruction and Systolic Anterior Motion of the Mitral Valve after Mitral Valve Reconstruction for Myxomatous Valve Disease; Journal of the American College of Cardiology; Aug. 30, 1999, 9 pages, vol. 34, No. 7; Published by Elsevier Science Inc.
McQueen; David M. et al.; Heart Animations Computed by the Immersed Boundary Method; http://www.math.nyu.edu/faculty/peskin/myo3D/index.html; Copyright 2005, 2 pages, accessed Oct. 31, 2014.
Lang; Roberto M., et al.; Recommendations for Chamber Quantification; The European Society of Cardiology; Dec. 23, 2005, 30 pages; Published by Elsevier Ltd.
Tops; Laurens F., et al.; Noninvasive Evaluation of the Aortic Root with Multislice Computed Tomography, Implications for Transcatheter Aortic Valve Replacement; Journal of the American College of Cardiology; Dec. 16, 2007, 10 pages, vol. 1, No. 3; Published by Elsevier Science Inc.
Gijsen; Frank JH, et al.; Simulation of Stent Deployment in a Realistic Human Coronary Artery; Aug. 6, 2008, 11 pages; Published by BioMedical Engineering OnLine.
Schoenhagen; Paul, et al.; Three-Dimensional Imaging of the Aortic Valve and Aortic Root with Computed Tomography: New Standards in an Era of Transcatheter Valve Repair/Implantation; European Heart Journal; May 13, 2009, 8 pages; Published by the European Society of Cardiology.
Kurra; Vikram, et al.; Pre-Procedural Imaging of Aortic Root Orientation and Dimensions, Comparison Between X-Ray Angiographic Planar Imaging and 3-Dimensional Multidetector Row Computed Technology; The American College of Cardiology Foundation; Oct. 15, 2009, 9 pages, vol. 3, No. 1; Published by Elsevier Science Inc.
Schoenhagen; Paul, et al.; Three-Dimensional Imaging in the Context of Minimally Invasive and Transcatheter Cardiovascular Interventions using Multi-Detector Computed Tomography: From Pre-Operative Planning to Intra-Operative Guidance; European Heart Journal; Aug. 3, 2010, 15 pages; Published by the European Society of Cardiology.
Quaini; Annalisa, et al.; A Three-Dimensional Computational Fluid Dynamics Model of Regurgitant Mitral Valve Flow: Validation Against In Vitro Standards and 3D Color Doppler Methods; Cardivascular Engineering and Technology; Feb. 8, 2011, 13 pages.
Mihalef; Viorel, et al.; Patient Specific Modelling of Whole Heart Anatomy, Dynamics and Haemodynamics from Four-Dimensional Cardia CT Images; Interface Focus; Mar. 23, 2011, 12 pages.
Jelnin; Vladimir, et al.; Clinical Experience with Percutaneous Left Ventricular Transapical Access for Interventions in Structural Heart Defects, A Safe Access and Secure Exit; The American College of Cardiology Foundation; May 31, 2011, 7 pages, vol. 4, No. 8; Published by Elsevier Inc.
Jabbour; Andrew, et al.; Multimodality Imaging in Transcatheter Aortic Valve Implantation and Post-Procedural Aortic Regurgitation, Comparison Among Magnetic Resonance Cardiac Computed Tomography, and Echocardiography; The American College of Cardiology Foundation; Sep. 13, 2011, 9 pages, vol. 58, No. 21; Published by Elsevier Inc.
Schievano; Silvia, et al.; Finite Element Analysis to Study Percutaneous Heart Valves; UCL Institute of Cardiovascular Science; Mar. 30, 2012, 27 pages; Published by InTech.
Achenbach, Stephan, et al.; SCCT Expert Consensus Document on Computed Tomography Imaging Before Transcatheter Aortic Valve Implantation (TAVI)/Transcatheter Aortic Valve Replacement (TAVR); Journal of Cardiovascular Computed Tomography; Nov. 6, 2012, 15 pages.
Borazjani; Iman, et al.; Left Ventricular Flow Analysis: Recent Advances in Numerical Methods and Applications in Cardiac Ultrasound; Mar. 19, 2013, 12 pages; Hindawi Publishing Corporation.
Litmanovich; Diana E., et al.; Imaging in Transcatheter Aortic Valve Replacement (TAVR): Role of the Radiologist; Insights Imaging; Jan. 21, 2014, 23 pages.
Fast App: Looking Deep into Heart Valve Replacement; http://www.deskeng.com/de/fast-app-looking-deep-into-heart-valve-replacement; Feb. 12, 2014, 4 pages, accessed Oct. 31, 2014.
Guerrero; Mayra, et al.; First in Human Percutaneous Implantation of a Balloon Expandable Transcatheter Heart Valve in a Severly Stenosed Native Mitral Valve; Feb. 15, 2014, 5 pages.
Griffith; Boyce E.; Multi-Beat Simulations of the Fluid Dynamics of the Aortic Heart Valve with Physiological Driving and Loading Conditions using the Immersed Boundary Method; http://www.cims.nyu.edu/~griffith; Jul. 4, 2014, 14 pages, accessed Oct. 31, 2014.
University of California, Health Sciences; Doctors use 3D Printed Model to Guide Tricky Heart Valve Replacement; ScienceDaily; Jul. 1, 2015, 3 pages.

* cited by examiner

METHOD OF ANALYZING HOLLOW ANATOMICAL STRUCTURES FOR PERCUTANEOUS IMPLANTATION

CROSS REFERENCE TO RELATED APPLICATIONS

This application claims the benefit of U.S. Provisional Application No. 62/034,251 filed Aug. 7, 2014, the entire contents of which are hereby incorporated by reference.

TECHNICAL FIELD

The present disclosure is generally related to periprocedural planning methods, and more specifically, but not exclusively, to methods of analyzing hollow anatomical structures and planning for successful percutaneous implantation.

BACKGROUND

Non-invasive percutaneous implantation of stents, prosthetic valves, and other like implantable devices poses certain challenges for physicians. As opposed to surgically invasive procedures, such as open heart surgery, for example, physicians performing non-invasive percutaneous implantation procedures have a limited field of view and are generally limited to the use of two-dimensional (2D) imaging modalities (e.g., fluoroscopy, ultrasound, etc.) during the procedure. Accordingly, periprocedural planning for non-invasive procedures that involves advanced imaging strategies can lead to more successful percutaneous implantation outcomes.

In the field of cardiology, transfemoral, transapical, and transaortic implantation are promising alternatives to open heart surgery, particularly for inoperable and high surgical risk patients. However, because physicians are typically limited to 2D imaging during the procedure itself, proper planning and evaluation is required to accurately size the target vessel or chamber, choose an appropriately sized implant, and determine both an ideal position for the implant and a point of access into the patient's body for performing the implantation. Failure to accurately size the target vessel or chamber, choose the appropriately sized implant, and determine an ideal position for the implant and a point of access can result in, for example, valve regurgitation, laceration of the patient's native blood vessels, lungs, or other anatomical structures, and/or fatal pericardial tamponade.

SUMMARY

According to one embodiment, there is provided a method of analyzing a hollow anatomical structure of interest for percutaneous implantation. The method comprises acquiring image data relating to an anatomical region of interest that at least partially includes the anatomical structure of interest, and generating a segmented model of the anatomical region of interest using the acquired image data. The method further comprises obtaining one or more images of the anatomical structure of interest by sectioning out intervening anatomical structures from the segmented model. The method still further comprises identifying one or more pertinent landmarks of the anatomical structure of interest in the one or more acquired images, and measuring at least one of a circumference, a maximal diameter, or a minimal diameter of one or more features of the anatomical structure of interest contained in the one or more acquired images to determine an anatomical structure size. The method yet still further comprises reconciling the anatomical structure size and an implant size.

According to another embodiment, there is provided a method of analyzing a hollow anatomical structure of interest for percutaneous implantation. The method comprises acquiring a model of an anatomical region of interest that at least partially includes the anatomical structure of interest, wherein the model is generated from image data relating to the anatomical structure of interest. The method further comprises obtaining one or more images of the anatomical structure of interest by sectioning out intervening anatomical structures from the model, and acquiring data relating to the anatomical structure of interest from the one or more images of the anatomical structure of interest. The method still further comprises determining a size of an implant to be implanted into the anatomical structure of interest based on the acquired data.

According to yet another embodiment, there is provided a non-transitory, computer-readable storage medium storing instructions thereon that when executed by one or more electronic processor(s) causes the processor(s) to carry out one or more steps of the method of: acquiring a model of an anatomical region of interest that at least partially includes the anatomical structure of interest, wherein the model is generated from image data relating to the anatomical structure of interest; obtaining one or more images of the anatomical structure of interest by sectioning out intervening anatomical structures from the model; acquiring data relating to the anatomical structure of interest from the one or more images of the anatomical structure of interest; and determining a size of an implant to be implanted into the anatomical structure of interest based on the acquired data.

BRIEF DESCRIPTION OF DRAWINGS

One or more embodiments of the invention will hereinafter be described in conjunction with the appended drawings, wherein like designations denote like elements, and wherein.

DETAILED DESCRIPTION OF THE ILLUSTRATED EMBODIMENT(S)

The method described herein can assist physicians in pre-operational planning and post-operative evaluation (also referred to as "periprocedural planning") of various percutaneous procedures. Generally, the method includes the use of advanced imaging and modeling strategies to accurately size the target hollow anatomical structure (e.g., valve, vessel, etc.), choose an appropriately sized implant, and/or determine an ideal position for the implant and/or a point of access into the patient's body for performing the percutaneous implantation. Although the method may be applicable to planning for and evaluating a variety of percutaneous procedures, it is particularly applicable to cardiac procedures, and even more particularly, cardiac procedures involving the mitral valve. Accordingly, a predominant portion of the discussion below is directed to analysis of the mitral annulus for transcatheter mitral valve replacement (TMVR). However, it should be understood that the various teachings could be applied to any number of percutaneous implantation procedures directed to different hollow anatomical structures, for example, procedures directed to the aorta, the left atrial appendage, the inferior vena cava, or any other vessel or chamber.

A non-invasive, percutaneous approach to TMVR has been reported in Guerrero et al., "First in Human Percutaneous Implantation of a Balloon Expandable Transcatheter Heart Valve in a Severely Stenosed Native Mitral Valve," Catheterization and Cardiovascular Interventions, 83:E287-E291 (2014), the contents of which are incorporated herein by reference in their entirety. An improperly sized replacement valve or improper placement of a valve during TMVR can lead to valve leakage and other deleterious effects. Moreover, procedures for mitral valve conditions such as severe mitral stenosis may posit certain challenges that might not be applicable to the aortic valve and other valves that are more simply or regularly shaped and distinguishable in operation.

Figure 1:
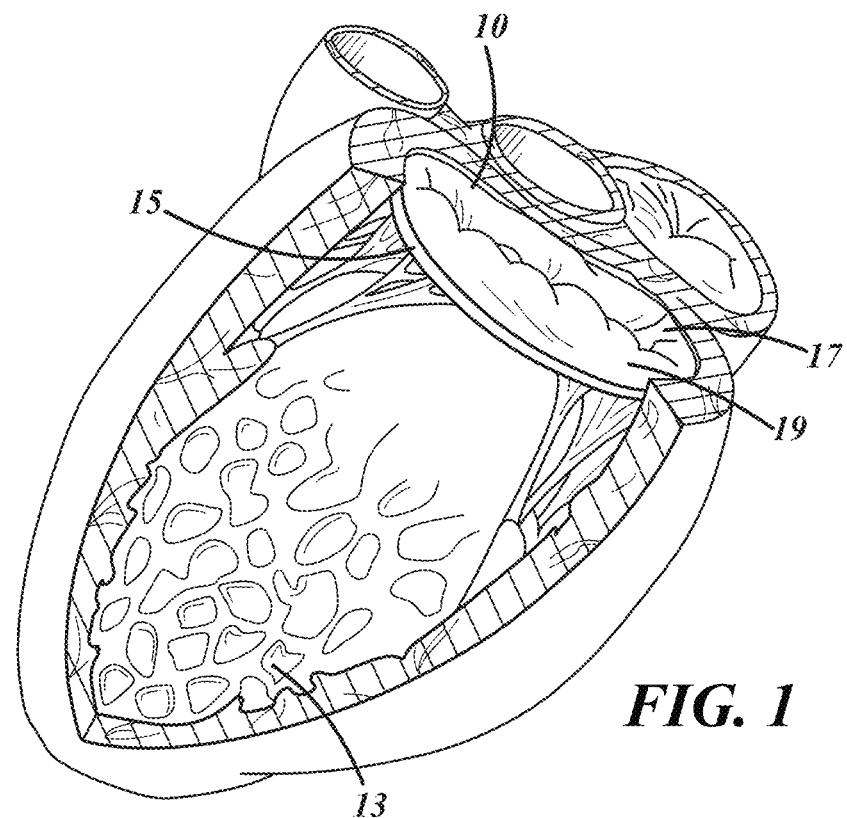
FIG. 1 schematically and diagrammatically shows the structure of a portion of the human heart.
Figure 2:
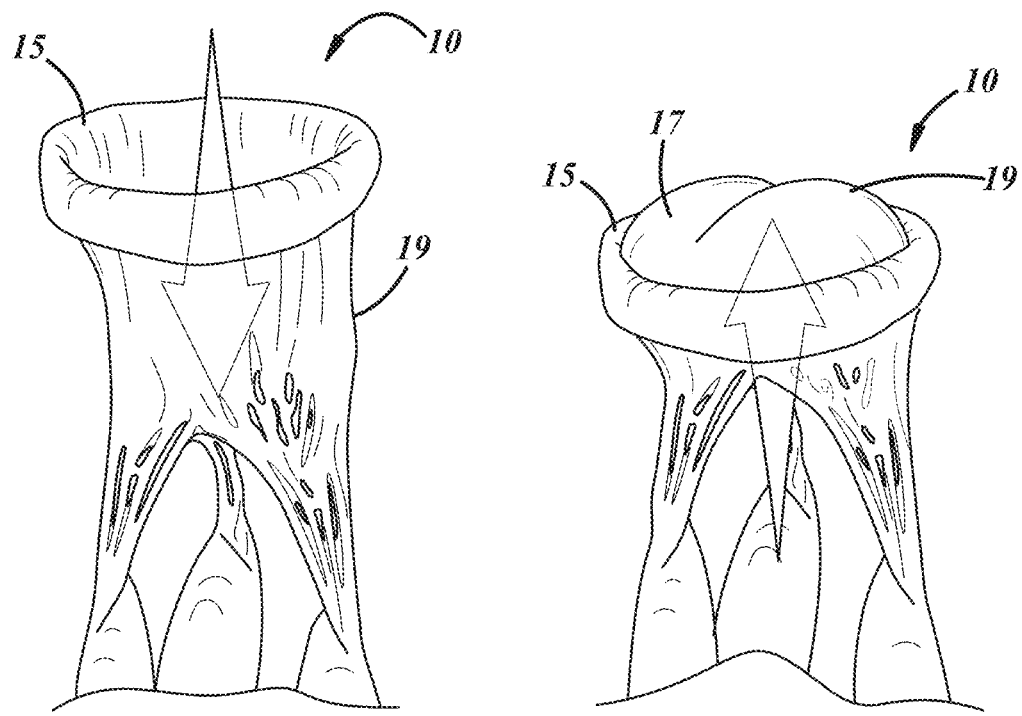
FIG. 2 is a schematically shows the operation of the mitral valve of a human heart.
Figure 3A:
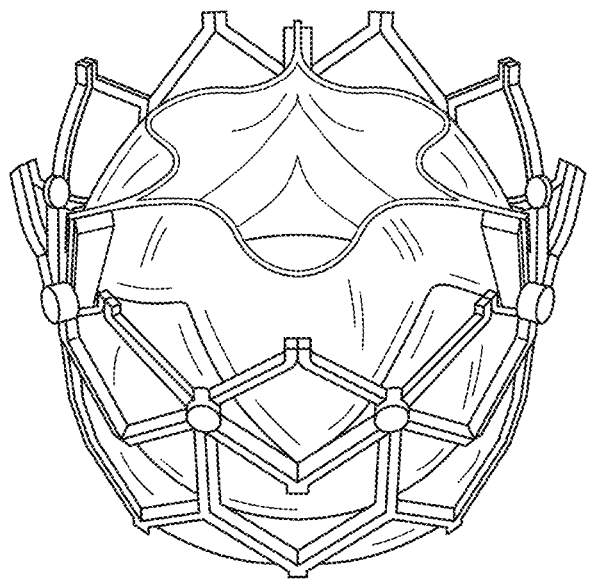
FIGS. 3A-3J depict examples of prosthetic heart valves that can be used during percutaneous implantation procedures.
Figure 3B:
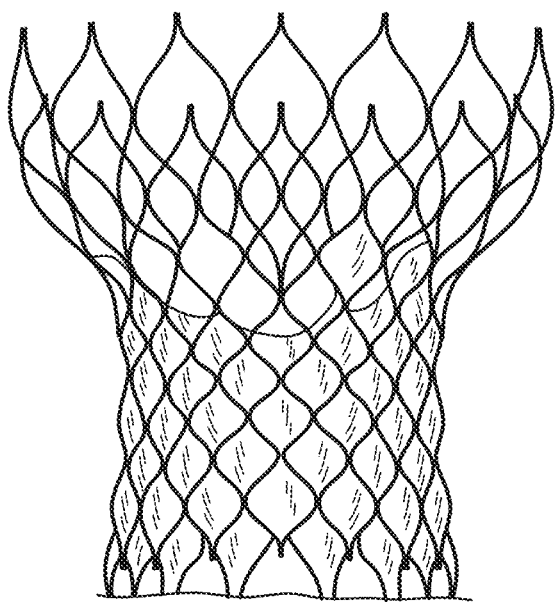
Figure 3C:
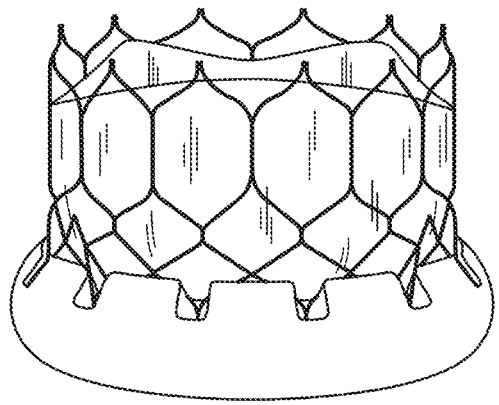
Figure 3D:
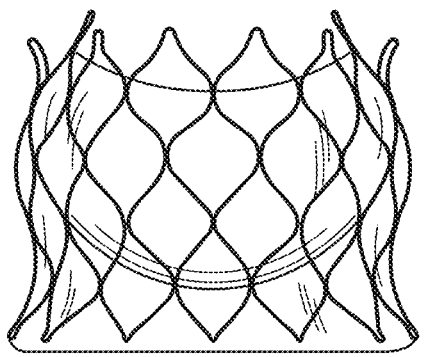
Figure 3E:
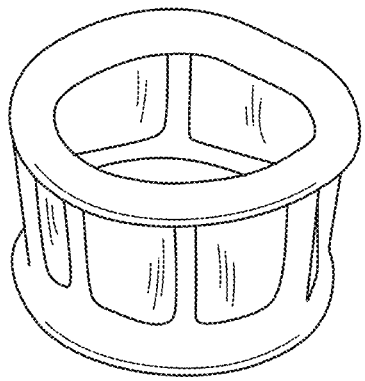
Figure 3F:
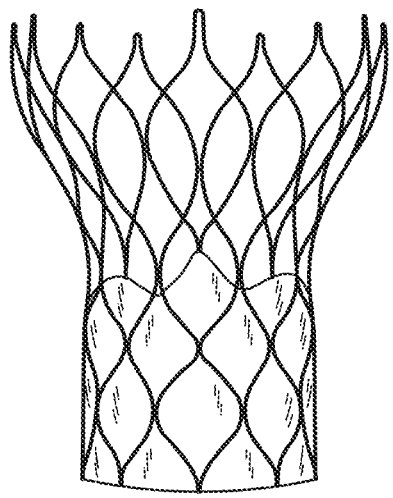
Figure 3G:
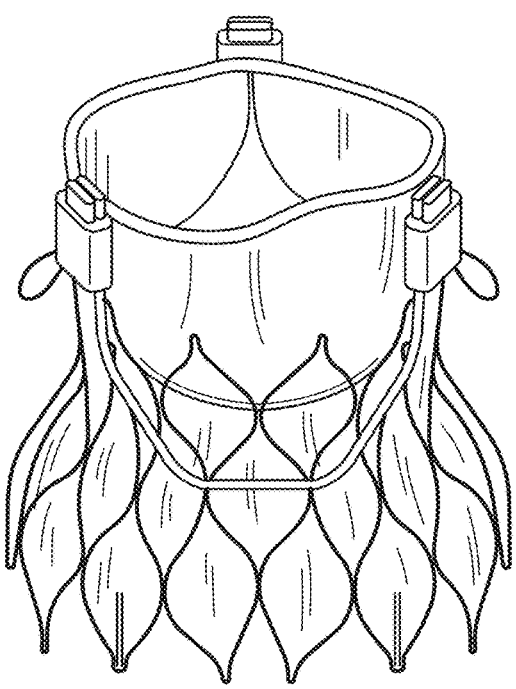
Figure 3H:
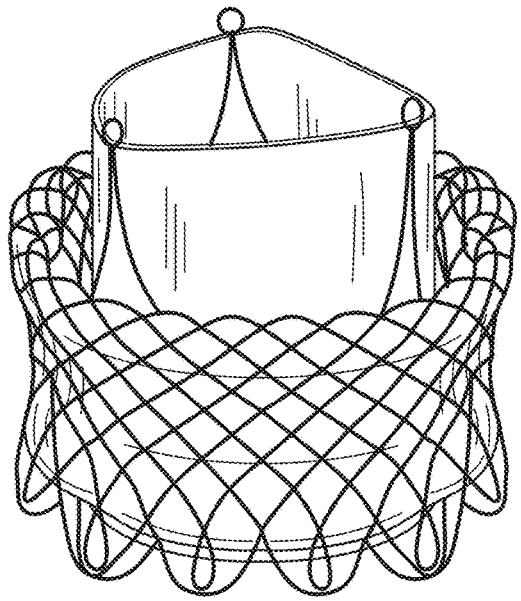
Figure 3I:
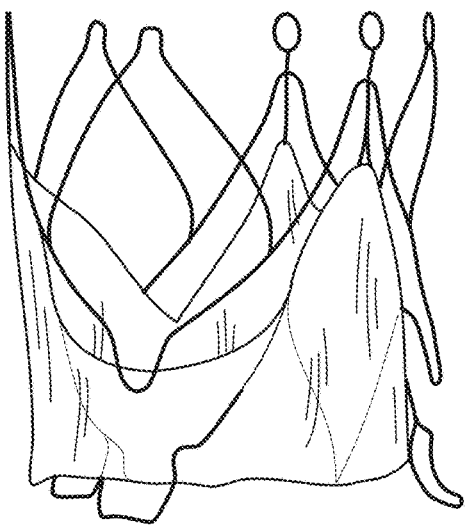
Figure 3J:
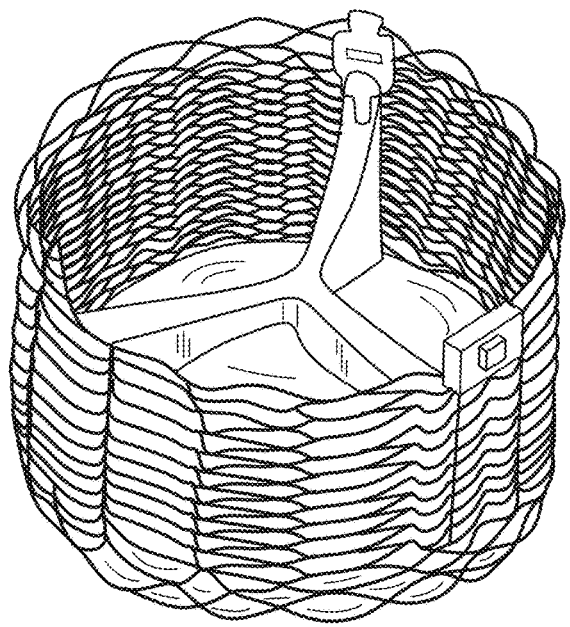

FIGS. 1 and 2 depict a mitral valve 10. As the mitral valve opens, an asymmetric toroidal vortex forms during the early diastolic phase of the cardiac cycle as blood flows from the left atrium (not shown) to the left ventricle 13. The unique saddle shape of the annulus 15 of the mitral valve changes during the cardiac cycle, as it is largest in the diastolic phase when the valve is open and smallest in the systolic phase when the valve is closed. Unlike the aortic valve which is gated by three leaflets, the mitral valve is gated by two leaflets: an anterior leaflet 17 and a posterior leaflet 19. Accurate sizing and placement of replacement or prosthetic mitral valves requires measurements of these native mitral valvular structures, particularly in light of the relatively large number of various replacement valves that are potentially available to physicians. A few examples of prosthetic mitral valves are depicted in FIGS. 3A-3J; though it will be appreciated that the present disclosure is not intended to be limited solely to those examples shown in FIGS. 3A-3J. Such a variety in prosthetic valve shapes is only beneficial if the mitral annulus is accurately sized and a precise location for placement of the prosthetic valve is determined.

Figure 4:
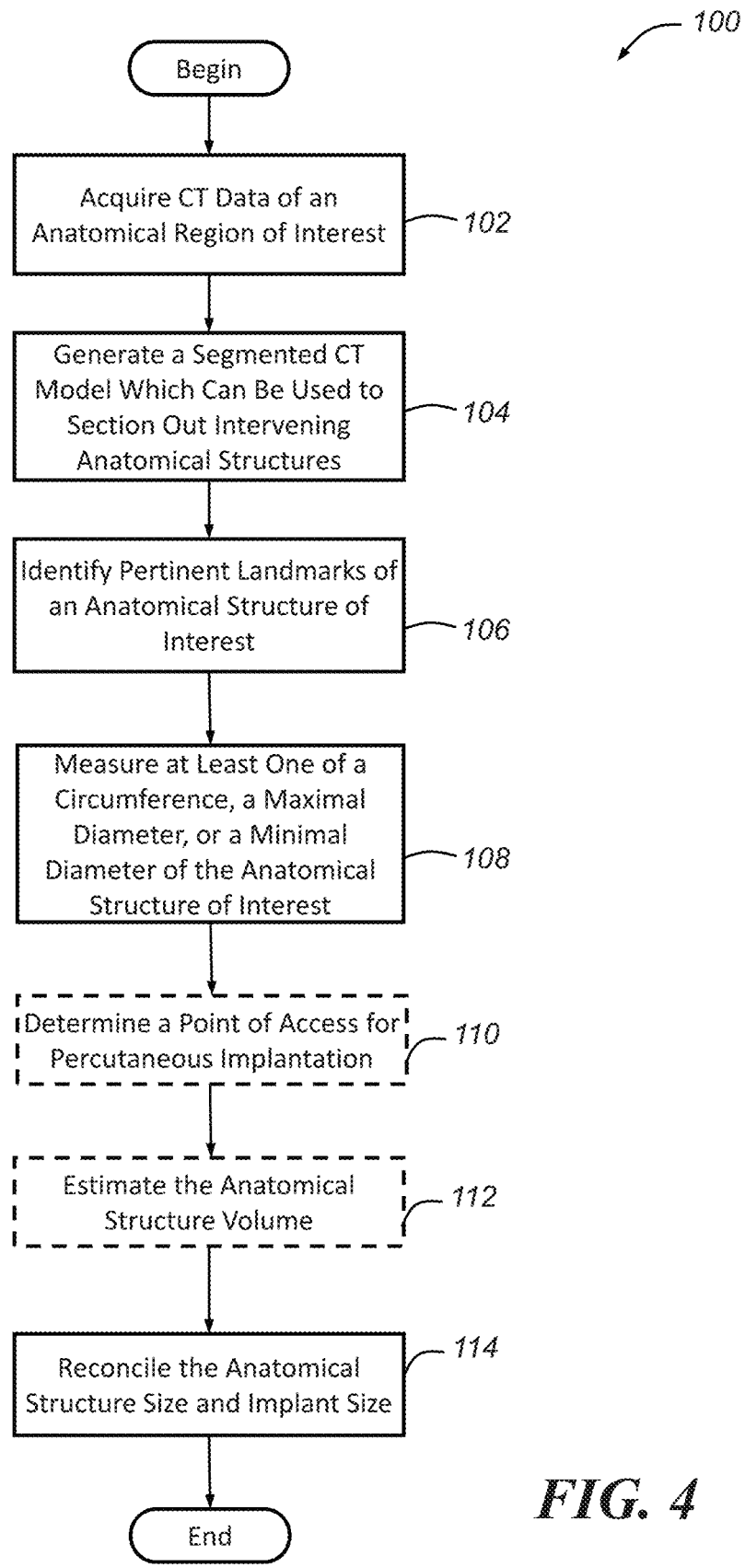
FIG. 4 is a flowchart of an illustrative embodiment of a method that may be used to analyze hollow anatomical structures (e.g., valves, vessels, etc.) for percutaneous implantation procedures.

Turning now to FIG. 4, there is shown an embodiment of a method 100 for analyzing a hollow anatomic structure (e.g., a vessel, valve, etc.) of interest for non-invasive percutaneous implantation procedures. As previously mentioned, the method will generally be described in the context of the mitral annulus and a percutaneous TMVR procedure. However, as also previously mentioned, it may be possible to apply the same or similar methodology to a variety of hollow anatomical structures and different percutaneous implantation procedures. According to one embodiment, some or all of the method steps are automatically performed using a system described more fully below and shown generally in FIG. 34; alternatively, some or all of the steps may be performed by a combination of the system described below and a user (e.g., a physician).

Beginning with step 102, image data relating to an anatomical region of interest that at least partially includes the anatomical structure of interest is acquired. In an illustrative embodiment, the image data comprises computed tomography (CT) image data, and more particularly, two-dimensional (2D) CT data. It will be appreciated, however, that in other embodiments, the image data may comprise data acquired using an imaging modality other than CT, for example, magnetic resonance imaging (MRI), echocardiogram imaging, or another suitable imaging modality. Accordingly, that the present disclosure is not intended to be limited to any particular type of image data. For purposes of illustration and clarity, however, the description below will be primarily with respect to image data in the nature of CT image data.

In any event, for a transapical TMVR procedure or a transapical transcatheter aortic valve replacement (TAVR) procedure, for example, the anatomical region of interest is generally the thoracic cavity. In one particular embodiment, step 102 includes taking a preliminary non-contrast CT scan to calculate the number of segments or slices needed to cover the field of view. For a transapical procedure, the lung apices and the apex of the heart should be included in the field of view. To acquire CT data of the anatomical region of interest, a contrast is administered to a patient. The contrast may be administered, for example, via an 18 or 20 gauge intravenous (IV) catheter placed in the right forearm. For cardiac procedures, an electrocardiogram (EKG) may also be used to monitor the heart. The CT data should be acquired during an inspirational breath-hold because such an expansion of the thoracic cavity presents a scenario where it is more likely that the lungs will obstruct the devices (e.g., a guide wire, a catheter, etc.) used during the procedure. During the procedure, patients are typically intubated to hold inspiration. Accordingly, the lungs hold less air during the procedure than during the pre-procedural scan which creates a safety margin of error between the inspirational breath-hold and a mechanically ventilated end-expiration state.

In step 104, a 3D model is generated from the image data acquired in step 102. Accordingly, in an embodiment, the 2D CT image data acquired in step 102 is utilized to generate or create a 3D CT model of the anatomical region of interest. The 3D model generated in step 104 may be, for example, a segmented 3D model that can be used or manipulated to section out intervening anatomical structures in order to obtain or acquire one or more images (e.g., 2D images) of the anatomical structure of interest. To perform this step, the data (e.g., CT data) acquired in step 102 is sent to a workstation that includes 3D reconstruction imaging/modeling software such as a Vitrea® workstation available from Vital Images, Inc. having a place of business in Minnetonka, Minn. The image data may be sent in DICOM format through a local network to the workstation. The workstation may include graphics cards and may allow for real-time or substantially real-time reconstruction of a segmented 3D model (e.g. segmented 3D CT model) with corresponding 2D images of the anatomical region of interest. As discussed above, in an embodiment, the anatomical region of interest includes the anatomical structure of interest, which in a preferred embodiment, is the mitral valve. In this embodiment, the workstation allows for substantially real-time reconstruction of the mitral valve in different phases of the cardiac cycle, which affects the shape and size of the mitral annulus. Intervening anatomical structures that may be sectioned out by removing layers of the 3D model include, but are not limited to, skin, bone, lungs, heart, and pertinent coronary artery anatomy, and will vary depending upon the particular application. Pertinent coronary artery anatomy may include the left anterior descending artery, coronary bypass grafts if the patient has any, and any additional vessels of interest. In any event, the result of the sectioning out of intervening anatomical structures results in one or more images (e.g., 2D images) of the anatomical structure of interest.

Following step 104, method 100 may proceed to a step 106 of identifying pertinent landmarks of the anatomical structure of interest contained within the image(s) of the anatomical structure of interest acquired by sectioning the model generated in step 104. This may be accomplished, for example, by playing the images in a cine loop, though other means/techniques for identifying the landmark(s) of interest may additionally or alternatively be used. Pertinent landmarks applicable to any cardiac procedure may include, but are certainly not limited to, post-surgical clips, any devices that were previously implanted (e.g., pacing wires, electrodes, etc.), and mild to severe areas of calcification. The impact of calcification will be described in more detail with reference to step 112.

With reference to an embodiment involving the mitral valve, the cine loop created for step 106 may consist of images of the mitral annulus taken on the coronal two chamber view. The cine loop allows for visualization of the mitral annulus anatomy and pertinent landmarks such as the mitral valve leaflet tips and the insertion points of the mitral valve leaflets at the mitral annulus. In at least some implementations, identification should be done during the diastolic phase of the cardiac cycle, as the mitral annulus is largest in the diastolic phase. However, in an embodiment, all phases of the cardiac cycle are analyzed to account for the dynamic movement of the left ventricle (LV) myocardium contractility and the left atrium (LA) size and contractility.

For procedures relating to the aorta such as TAVR, pertinent landmarks for step 106 may include the ostium of the left main coronary artery, the ostium of the right coronary artery, the ostium of any bypassed grafts arising from the aorta. In an embodiment, landmark identification and measurements described below with respect to step 108 should be performed during the systolic phase of the cardiac cycle, as the aortic annulus is largest in the systolic phase. Implantation of the transcatheter valve can then be performed with guidance of c-arm angulation from the CT scan data set, as described in more detail below.

For procedures relating to the left atrial appendage, pertinent landmarks for step 106 may include, for example, the pulmonary veins, the location of the Coumadin ridge, the transverse pericardial sinus, the circumflex artery or similar artery that traverses adjacent to the appendage, the mitral valve, the left atrium, the interatrial septum, and the superior vena cava and inferior vena cava transition into the interatrial septum (to help identify the best coaxial angle to the left atrial appendage main lobe for device positioning). C-arm angulation, described below, will be assessed to give the best projection angles that provide maximal delineation and separation of the left atrial appendage and the left atrium for a grasping zone (e.g., for lariat procedures) or a landing zone (e.g., for insertion of an Amplatz device, Watchman device, or other suitable devices (e.g., suitable left atrial appendage occlusion devices).

For procedures relating to the inferior vena cava, such as heterotopic transcatheter tricuspid inferior vena cava valve implantation (TIVI), also known as caval valve implantation (CAVI), pertinent landmarks for step 106 may include the right atrium-inferior vena cava plane, the inferior vena cava ostium, and the first hepatic vein, to cite a few examples. Unlike TAVR procedures, there are no valve insertion cusp points to use as landmarks in sizing the right atrium-inferior vena cava junction. The nadir of the right atrium-inferior vena cava plane varies from patient to patient based on the geometry of the patient's coronary sinus plane during inferior vena cava dilatation. C-arm angulation may vary and should be assessed on a case-by-case basis, but in an illustrative embodiment, the C-arm projections are right anterior oblique (RAO) 33 and caudal 22.

Once the pertinent landmark(s) of the anatomical structure of interest are identified, step 108 of the method calls for measuring one or more parameters of one or more features of the anatomical structure of interest, which may include, for example, and without limitation, at least one of a circumference, a maximal diameter, or a minimal diameter of the anatomical structure of interest or a feature thereof. The measurements, which, in an embodiment, may be made or taken using the image(s) of the anatomical structure of interest obtained or acquired in step 104 (e.g., 2D image(s) resulting from the sectioning of the 3D model generated in step 104), are typically obtained or taken at locations corresponding to the pertinent landmarks identified in step 106, and may possibly be obtained or taken between the pertinent landmarks as well. The measurements may also be obtained or taken in different planes and at different angles. It should also be noted that at any time, it is possible to take snapshots or save different CT images or image sets for later use, such as for reference purposes or to create cine loops of various phases or stages.

Figure 5:
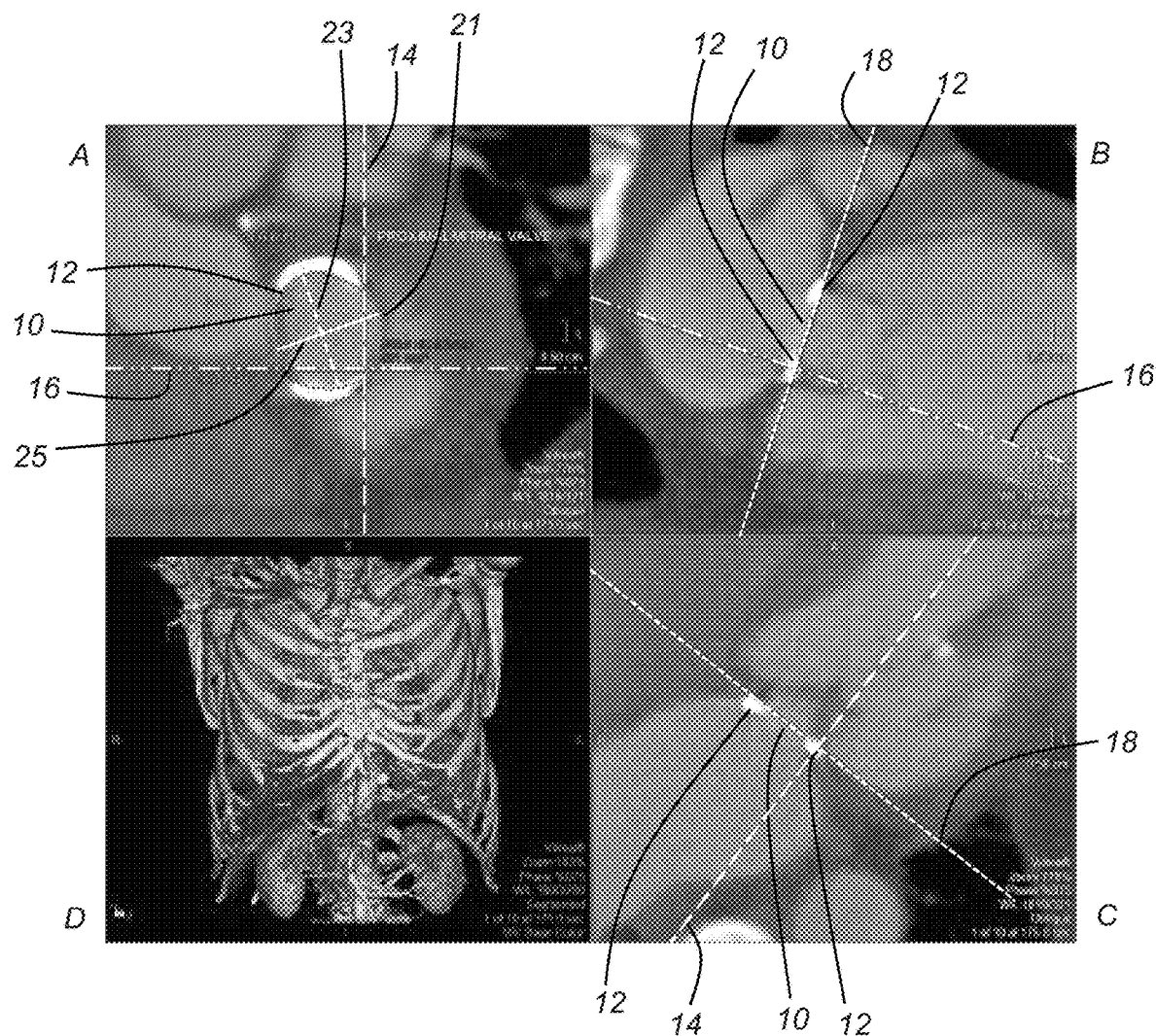
FIGS. 5-8 each comprise a three-dimensional (3D) model of the thoracic region of a patient acquired from an imaging system, and various images of a mitral valve acquired by sectioning the 3D model in different ways.
Figure 6:
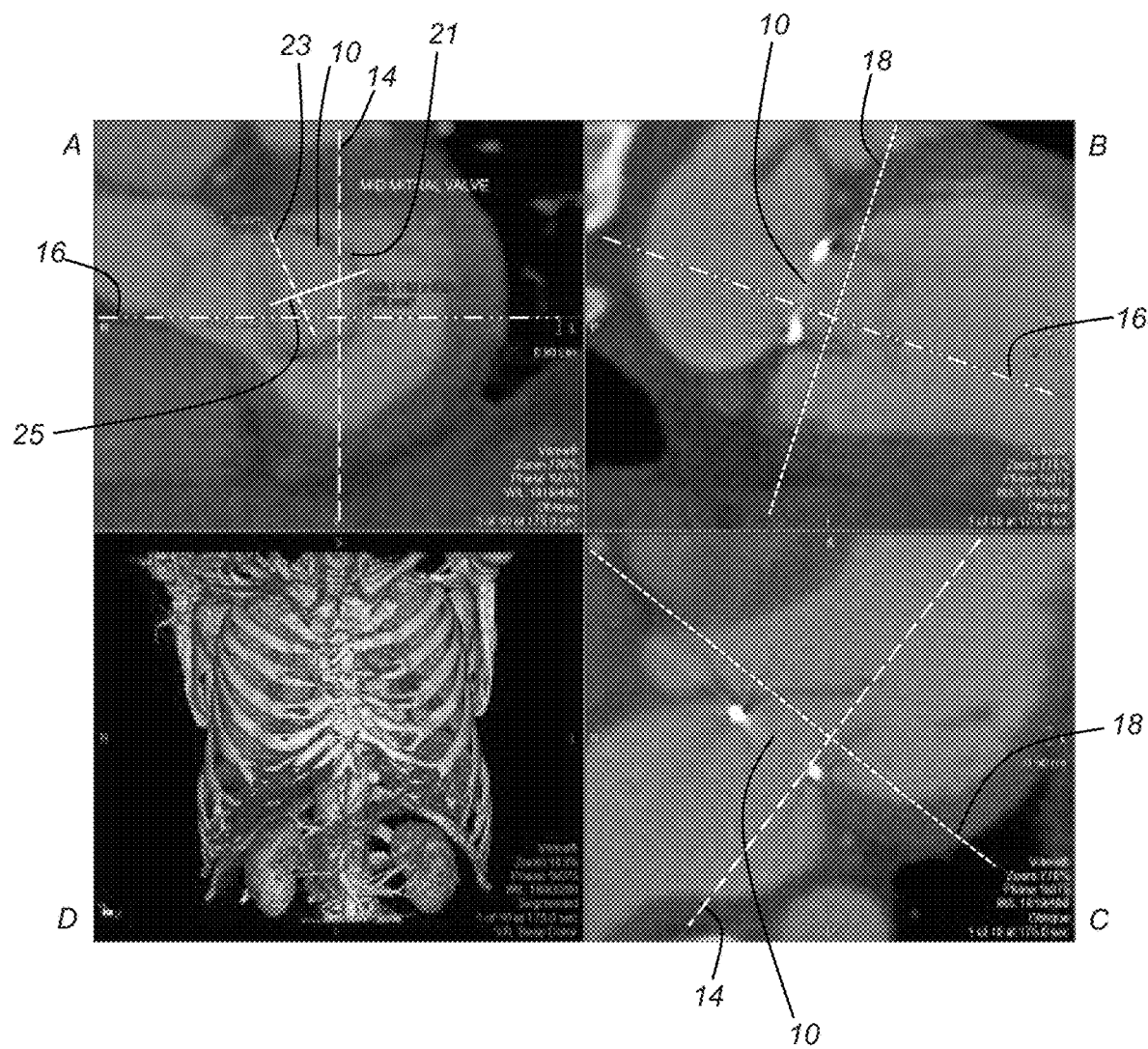
Figure 7:
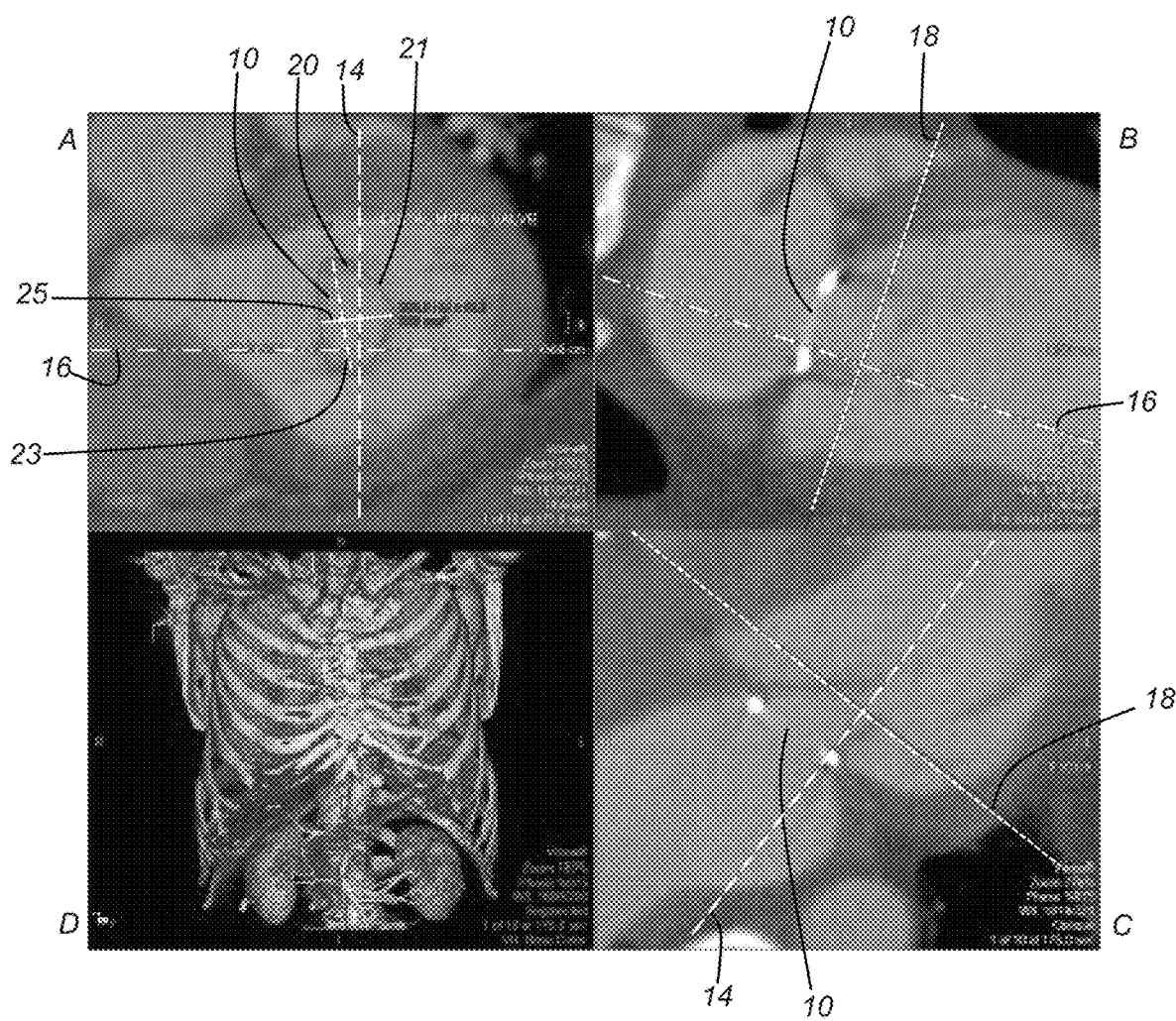

As a particular example, FIG. 5 shows a 3D CT model D of an anatomical region of interest (e.g., the thoracic region) and set of 2D CT images. The CT images comprise a first image taken along a sagittal plane (hereinafter "sagittal view A") of the 3D model D, a second image taken along a coronal plane (hereinafter "coronal view B") of the 3D model D, and a third image taken along an axial plane (hereinafter "axial view C") of the 3D model D. The sagittal view A comprises an image of a mitral valve 10 at a mitral valve leaflet insertion landmark 12. In the sagittal view A, there is a coronal plane indicator 14 and an axial plane indicator 16. The sagittal view A is acquired by aligning a sagittal plane indicator 18 in a coronal view B with the sagittal plane indicator 18 in an axial view C along the mitral valve 10. The alignment of the sagittal plane indicator 18 in the coronal and axial views B, C allows for a double oblique view to be produced of the mitral annulus in the sagittal view A. More details regarding the alignment of indicators to simulate the cardiac catheterization fluoroscopic projection are provided below. At this point, one or more measurements, for example, at least one of a circumference 21, a maximal diameter 23, or a minimal diameter 25 of the mitral annulus 15 may be taken in the sagittal view A, as shown. In one embodiment, a mean diameter is derived from the maximal diameter 23 and the minimal diameter 25. FIG. 6 is representative of a location at the midpoint of the mitral valve 10 between the leaflet insertion landmark 12 and a mitral valve leaflet tip landmark 20. FIG. 7 is representative of a location at the mitral valve leaflet tip landmark 20. The same or similar measurements such as those described above (e.g., with respect to FIG. 5) may be obtained at any or all of the locations depicted in FIGS. 5-7.

For the left atrial appendage, measurements for step 108 may include one or more of: the maximal and minimal diameter of the left atrium, the measurements of the ostium of the left atrial appendage (e.g., at least one of a maximal diameter, a minimal diameter, an area, or a circumference); the depth of the left atrial appendage to the first curvature of the left atrial appendage; the circumference, diameter (maximal and/or minimal), and area at the proposed site of device positioning within the left atrial appendage for optimal device deployment; the orientation of the left atrial appendage with respect to the left atrium (anterior or posterior facing); and the presence or absence of a left atrial appendage clot.

For the tricuspid inferior vena cava valve, measurements for step 108 may include one or more of the maximal and minimal diameter, area, and circumference at the right atrium-inferior vena cava plane, measured, in an embodiment, approximately 1 cm below the inferior vena cava ostium, and 1 cm above the first hepatic vein. Another measurement may include the vertical height between the inferior vena cava ostium and the first hepatic vein. It may be desirable to mark the inferior most landmark or area demonstrating the presence of regurgitant flow. In one embodiment, step 108 measurements for TIVI (or CAVI) procedures are taken while the patient is lying flat on a scanner table.

In any event, and as will be described below, the measurements of the anatomical structure of interest obtained in step 108 may be used to select a particularly sized implant, determine a point of access for percutaneous implantation, estimate the anatomical structure volume, generate a 3D CAD model of the anatomical structure of interest, generate a 3D printed model of the anatomical structure of interest, and/or evaluate a previously implanted device, for example Step 110 is optional and involves determining a point of access into the patient's body for percutaneous implantation. Since the method described herein is applicable to pre-operational planning and post-operational analysis, step 110 may only be necessary when the method is being used for pre-operational planning, and more particularly for transapical planning Typically, for transapical procedures, a point of access is attempted along the mid to distal anterolateral wall of the LV confirmed by a 2D transthoracic echocardiogram. Step 110 involves obtaining certain measurements that may better approximate an ideal point of access.

Figure 8:
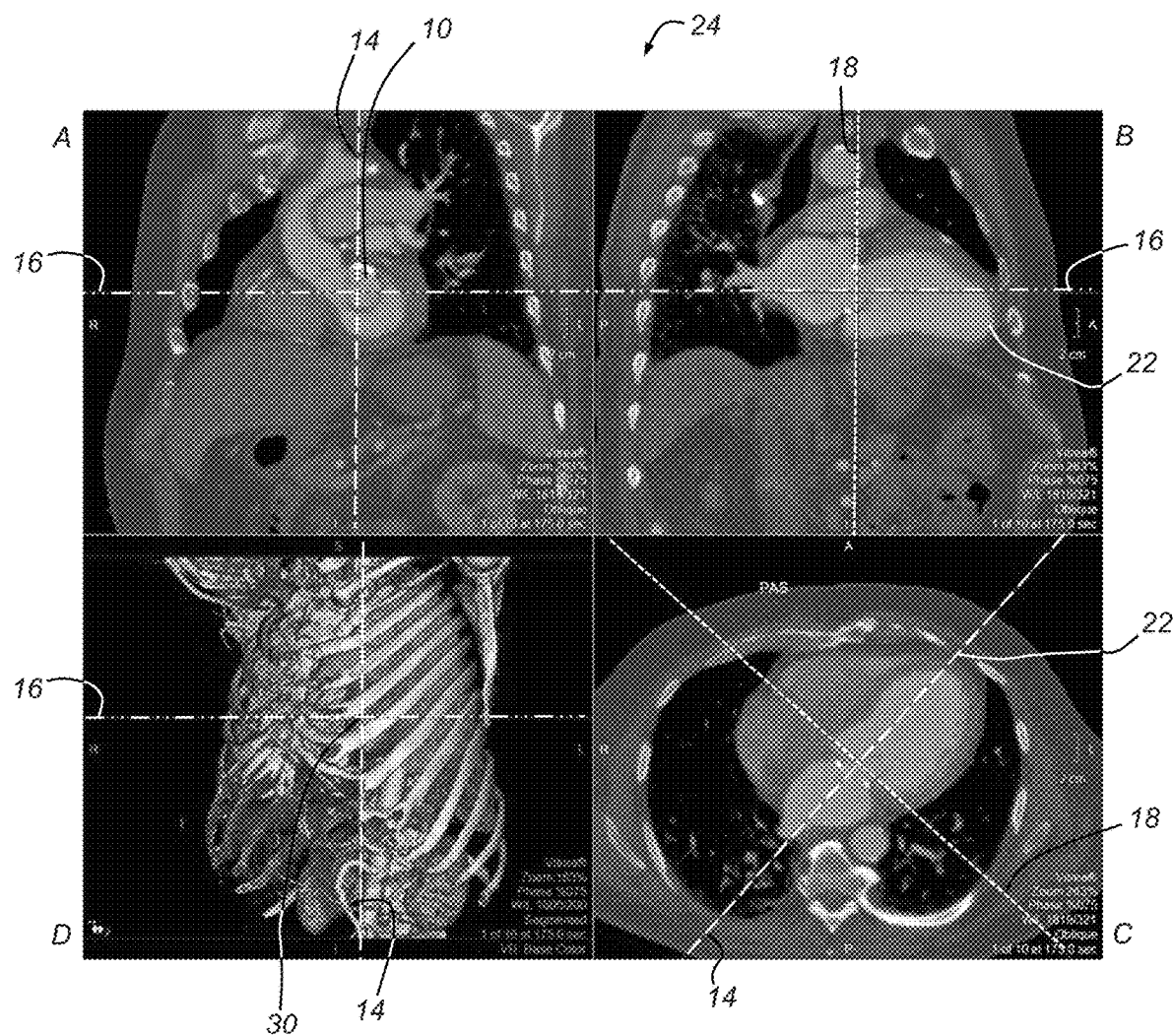

FIG. 8 shows a multiplane reformatted (MPR) image in the diastolic phase of the cardiac cycle, such as the one acquired in step 102. More particularly, like FIG. 5, FIG. 8 shows a 3D CT model D of an anatomical region of interest (e.g., the thoracic region) and set of 2D CT images. The CT images comprise a first image taken along a sagittal plane (hereinafter "sagittal view A") of the 3D model D, a second image taken along a coronal plane (hereinafter "coronal view B") of the 3D model D, and a third image taken along an axial plane (hereinafter "axial view C") of the 3D model D. It should be noted that in at least some implementations, all of the measurements described below with relation to step 110 should also be taken from an image while in the systolic phase of the cardiac cycle and then again in the diastolic phase to provide a range of cardiac contractility for feasibility of catheter placement. This allows the point of access to be represented in both phases, and a 3D cine loop of all ten phases of the cardiac cycle can be created with the lung fields and the point of access in view. In a particular embodiment, to prepare for a transapical percutaneous approach, the intersection of the coronal plane indicator 14 and the sagittal plane indicator 18 are generally aligned with the mitral valve 10, the mitral annulus 15, or a mitral prosthesis in the axial view C. More particularly, without angling any of the images, a potential point of access 30 can be identified during, for example, the diastolic phase of the cardiac cycle as the anterolateral region of the left ventricle that is believed to be free of the lungs, adjacent coronary vessels, ribs, and/or certain other anatomical structures on the axial plane. The plane in which the point of access 30 is disposed may then be aligned, manually or automatically, to be parallel to the blood flow of the left ventricle. In response to the identification or assignment of the point of access 30 and alignment of the point of access plane, the coronal and sagittal planes (and thus the corresponding plane indicators 14, 18) are automatically generated or identified. Then, in the axial view C, the intersection of the coronal plane indicator 14 and the sagittal plane indicator 18 may be angled such that one of the indicators runs parallel to the angle of the left ventricle (LV) apex 22. If while scrolling through the axial and coronal views, the proposed point of access 30 does not intersect any intervening anatomical structures that were identified/sectioned out in step 104, such as papillary muscles, ribs, vessels, or lung fields, for example, then this set of images will become a primary point of access image set 24. If the potential point of access 30 intersects with one of the intervening anatomical structures identified/sectioned out in step 104, a new potential point of access can be chosen by the user and the above process can be repeated to obtain the primary point of access image set 24. In an embodiment, the point of access 30 is assigned, selected, or identified by the user. It is contemplated, however, that in other embodiments, the identification of the point of access may be an automated process without requiring input from the user. Accordingly, the present disclosure is not intended to be limited to any particular way or technique of identifying the point of access 30.

Figure 9:
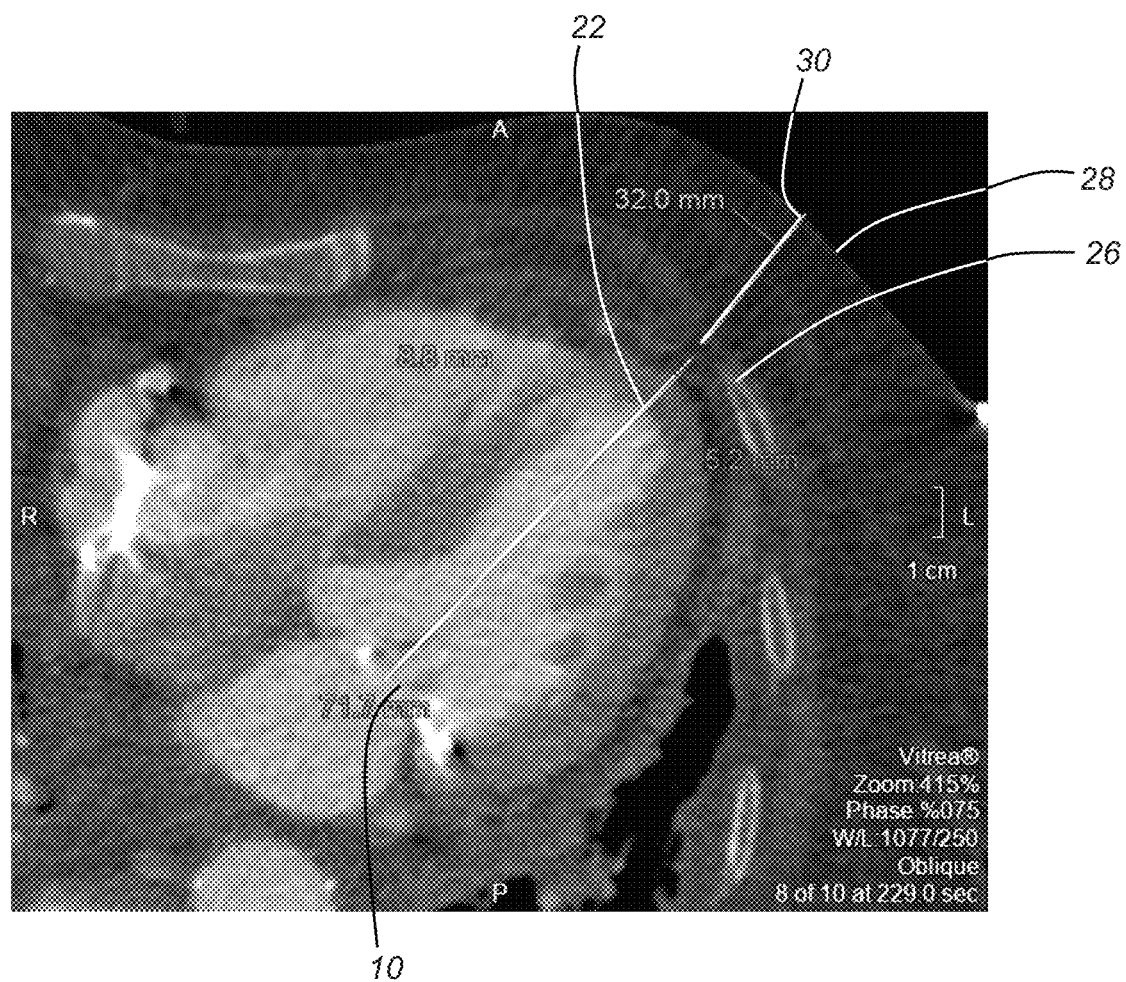
FIGS. 9-29 are images/models of various thoracic structures acquired from an imaging system.
Figure 10:
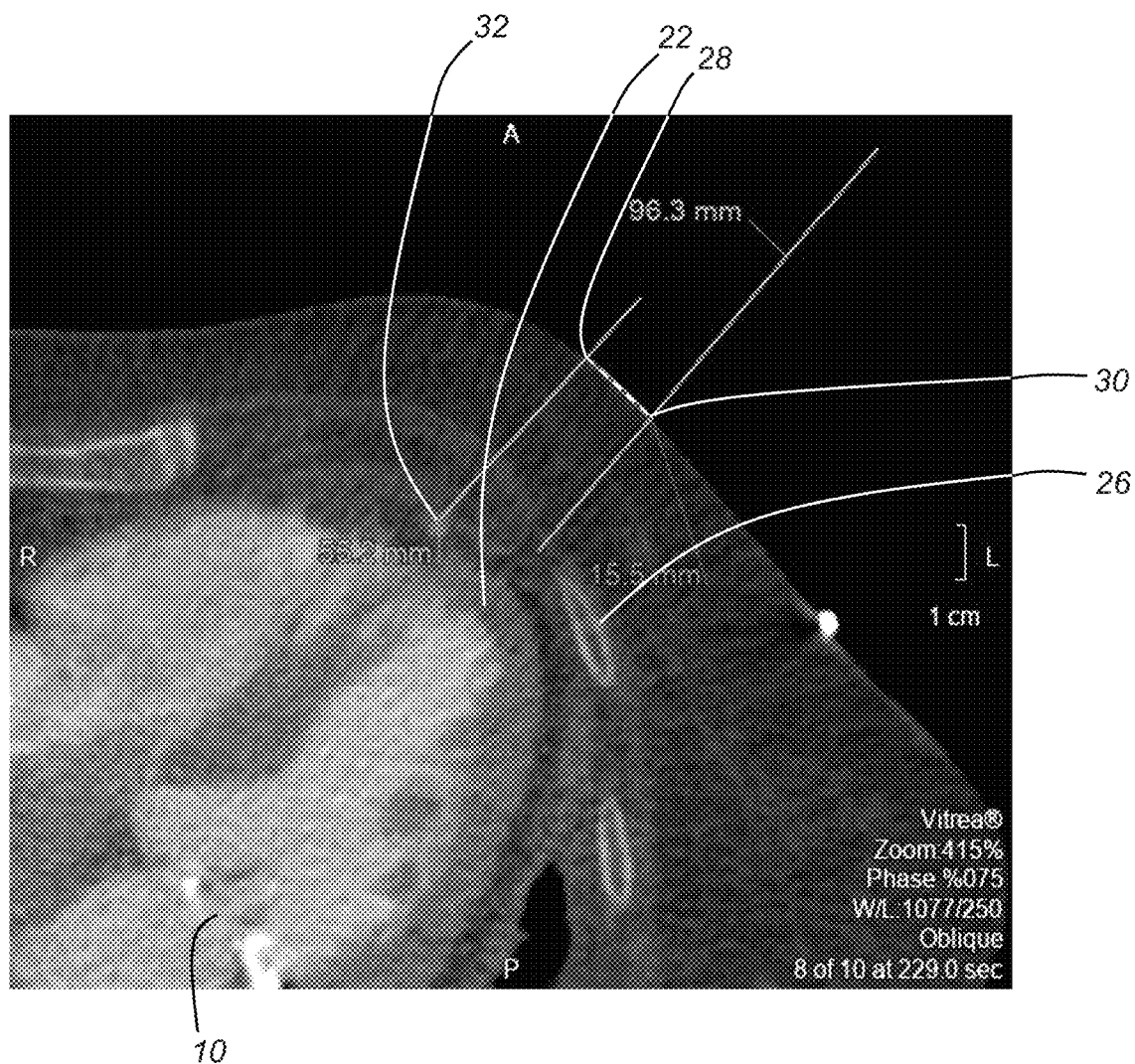
Figure 11:
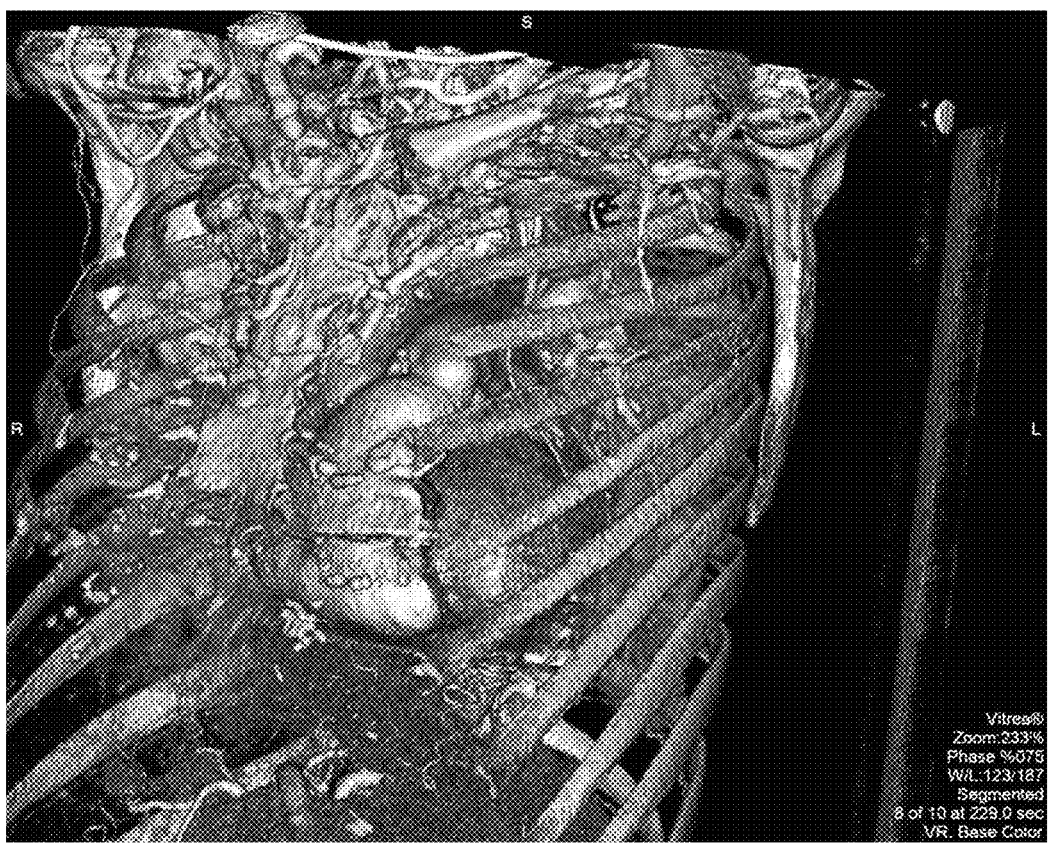

Other measurements may be obtained to verify the point of access 30 determined or identified in step 110 and assist the physician in other procedural aspects. For example, FIG. 9 is an image from the primary point of access image set 24. In this image, the distance from the center of the mitral annular plane of the mitral valve 10 to the endocardium at the LV apex 22 is measured. This distance may impact the physician's choice of sheath length as well as catheter and wire sizing, for example. As another example, the distance between ribs 26 and a surface of the skin 28 may assist in the assessment of the depth of the needle penetration. As shown in FIG. 10, it is possible to extend the measurement between the ribs 26 and the surface of the skin 28 out at the same angle as the direction of the LV apex 22. This measurement may be applied to a 3D reconstruction image/model, such as the image shown in FIG. 11, or a 3D reconstruction/model that includes a representation of the patient's skin in the model. This can provide the point of access trajectory from internal to the skin to the mitral annulus of the mitral valve 10 in a 3D model, which may be viewed in still form or in a cine loop.

In an embodiment, it is possible to manipulate the 3D model generated in step 104 to remove any intervening vessels such as the left anterior descending artery (LAD), the left internal mammary artery (LIMA), a potential bypass graft, for example, as well as any other intervening anatomical structures layer-by-layer. It may be beneficial to extend a line 32 (shown in FIG. 10) from the LAD substantially parallel to the point of access line to at least the surface of the skin 28. In an embodiment, line 32 is extended exactly parallel to the point of access line; in other embodiments, however, the lines may not be exactly parallel, but rather may be angled with respect to each other by a predetermined amount deemed suitable for the purposes described below. In any event, the distance between the line 32 and the point of access 30 above the surface of the skin 28 may be measured and that measurement may be used to estimate a distance between the trajectory path and the LAD. Knowing this distance may help to avoid unnecessary perforation of the LAD, for example. It may also be possible to angle the 3D model, such as the 3D model shown in FIG. 11, to show the distance more clearly. Other measurements may include the LV wall thickness as defined between the endocardium and the epicardium, and the epicardial fat thickness. It may also be beneficial to measure the maximal and minimal diameters of the left atrium (LA) while in the systolic phase and the interatrial septum length for the particular case where the transapical approach fails and a transseptal approach must be attempted instead.

Figure 12:
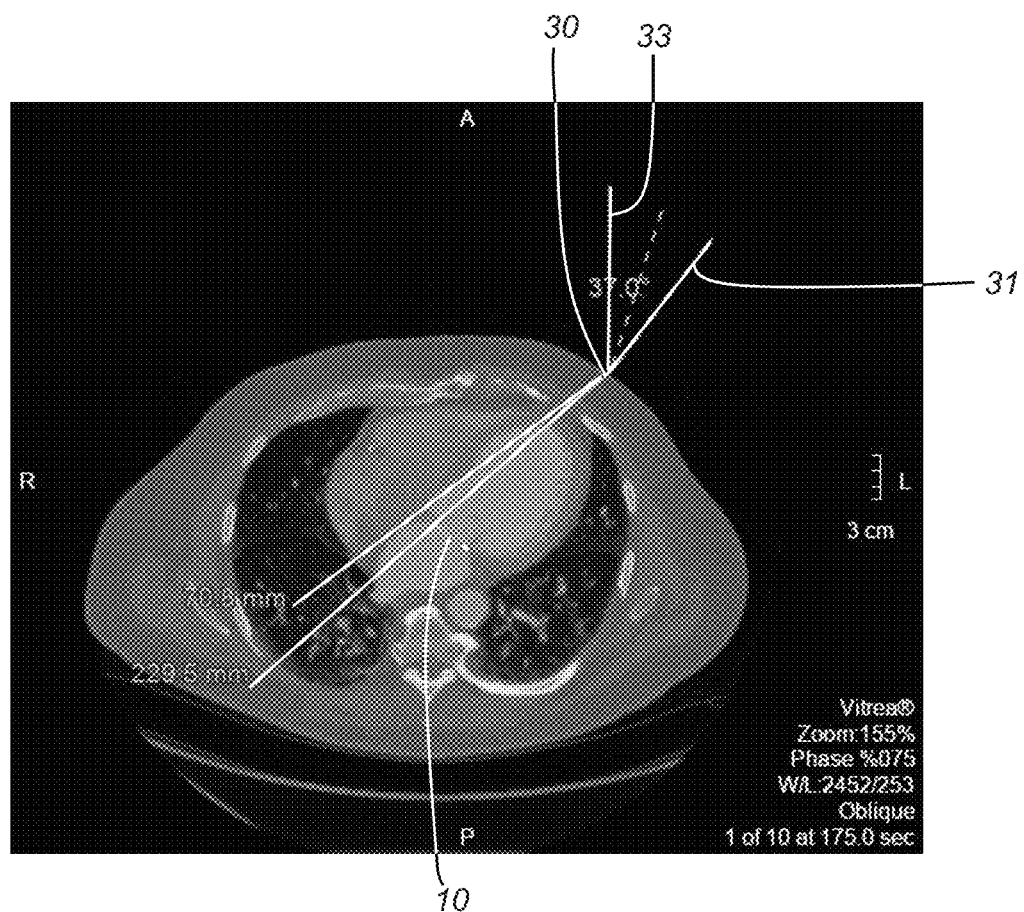
Figure 13:
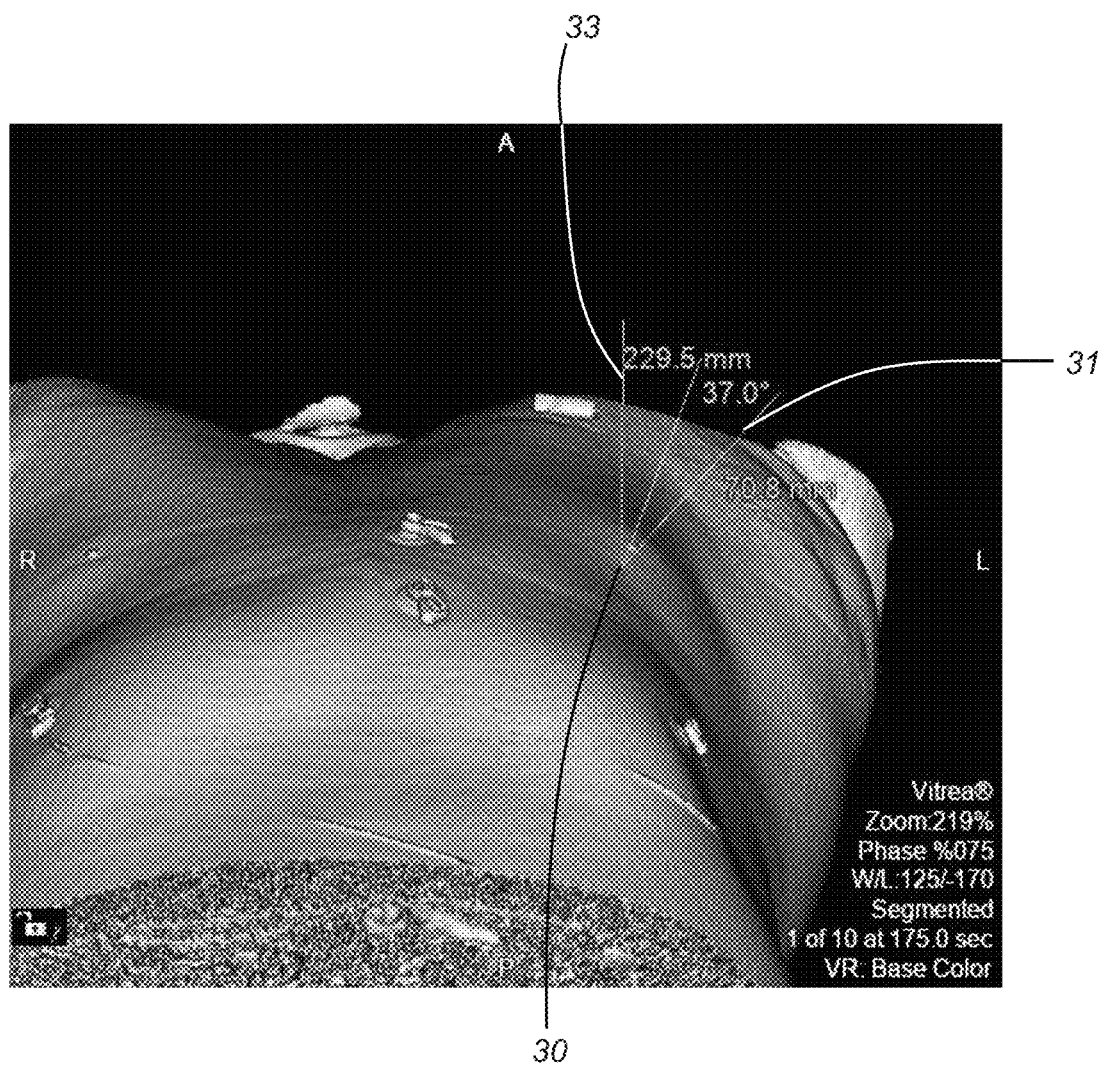

Another aspect that may be included in step 110 involves determining a trajectory angle at the point of access 30 and a corresponding C-arm deployment angle. With reference to FIGS. 12 and 13, a trajectory 31, and thus, the trajectory angle, may be determined by assuming a perpendicular plane 33 from, for example, an axial view/plane that extends orthogonally from the patient's spine, and angling only in a lateral direction (i.e., to the patient's left side). In an embodiment, the primary point of access image set 24 may be is used to generate the axial view, shown in FIG. 12, and the axial view with caudal angulation, shown in FIG. 13. The C-arm deployment angle may be generally defined by the point of access trajectory 31 and the plane 33. In the illustrated embodiment, the point of access trajectory angle is 37.0°, which may be shown on the 3D rendering as depicted in FIG. 13. The point of access trajectory may help with determining a C-arm deployment angle, as described later with reference to FIGS. 36 and 37. It will be appreciated, however, that in other embodiments, different angles may also be suitable for the point of access trajectory and C-arm deployment. Additionally, intraprocedural utilization of additional C-arm views may be provided to virtually simulate the needle position in different (e.g., two different) perpendicular vector views to demonstrate that the needle/catheter is coaxial to the mitral valve point of interest, and not angled in any direction towards pertinent anatomical structures. These pertinent structures, which may include, for example, coronary vessels, the mitral annulus, blood volume of the left ventricle, sternotomy wires, intracardiac devices, and other reproducible landmarks, will be generated in the C-arm overlay.

Figure 14:
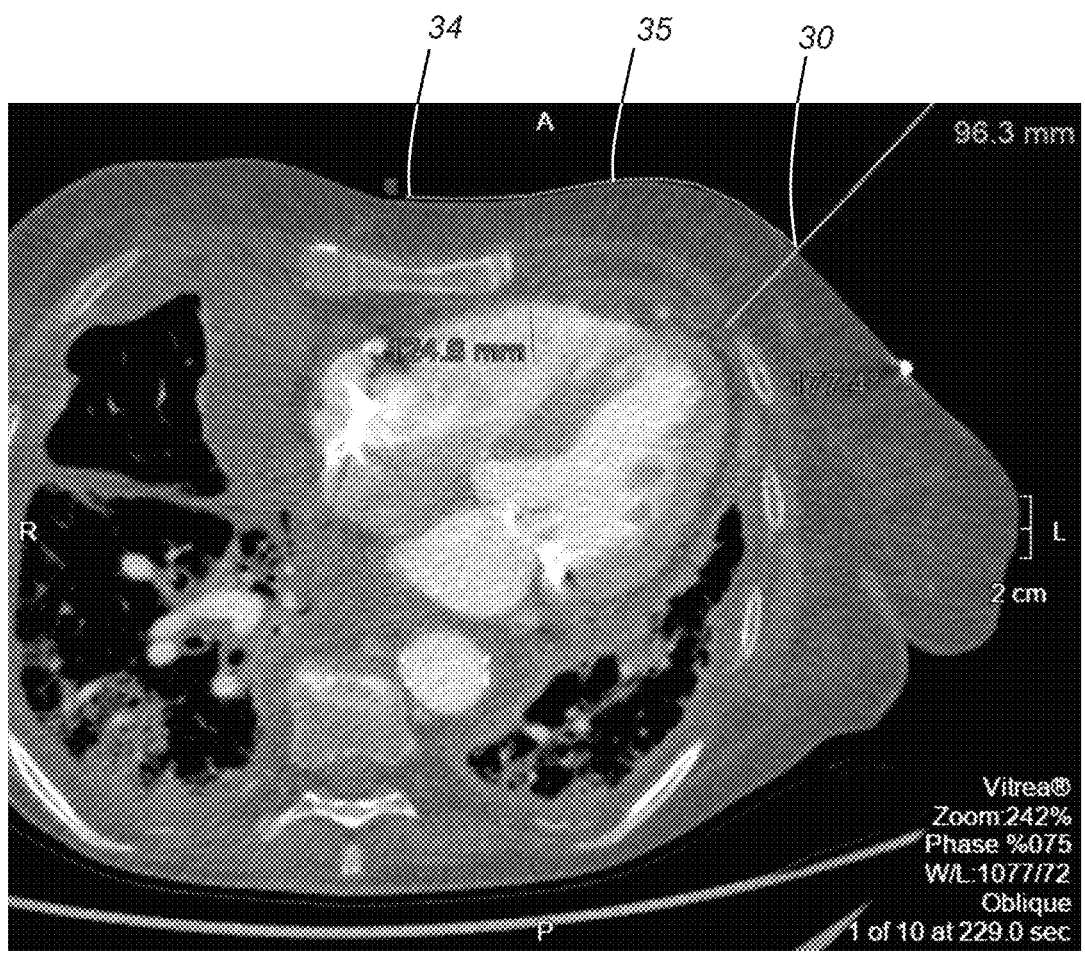
Figure 15:
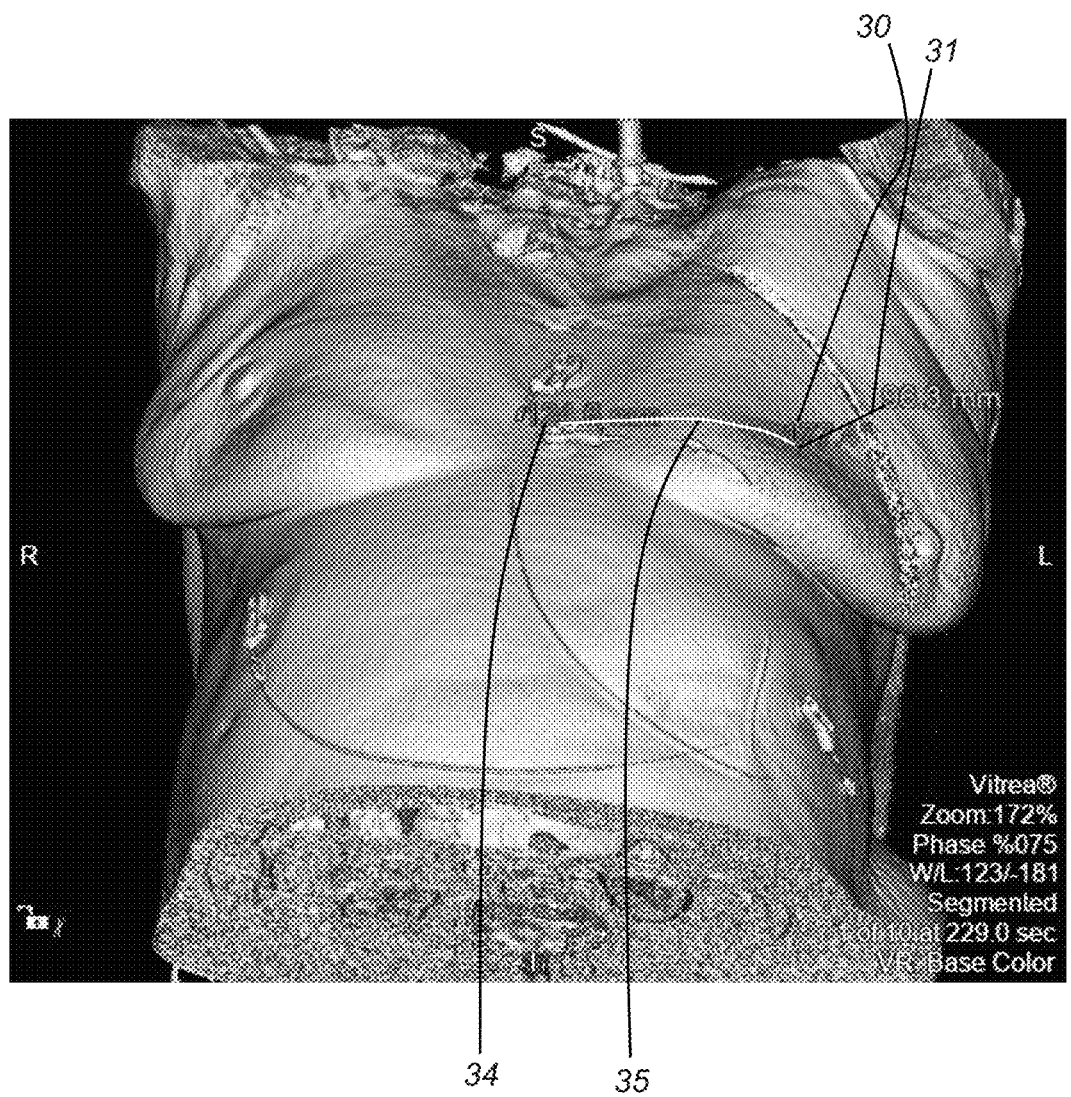
Figure 16:
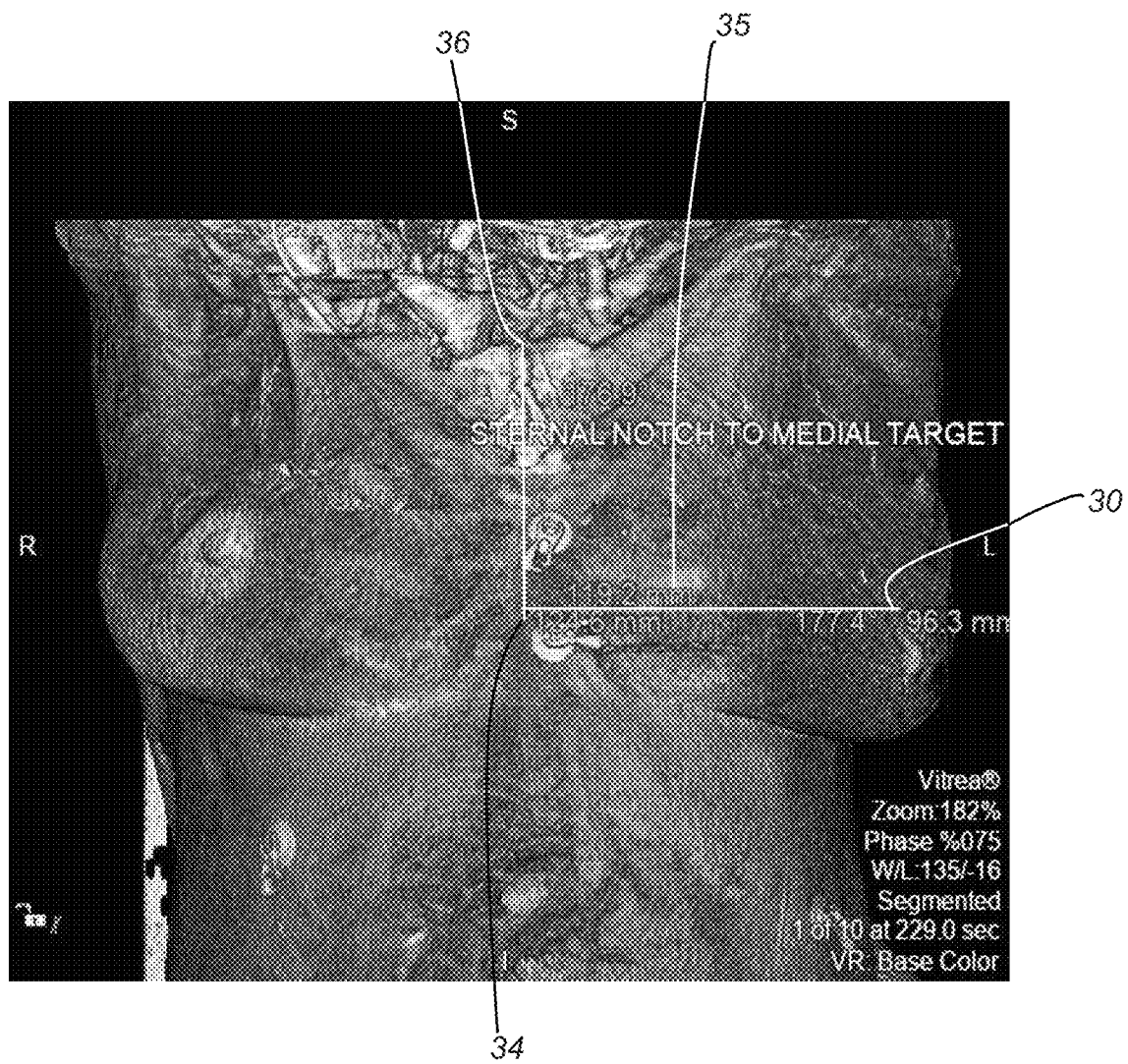
Figure 17:
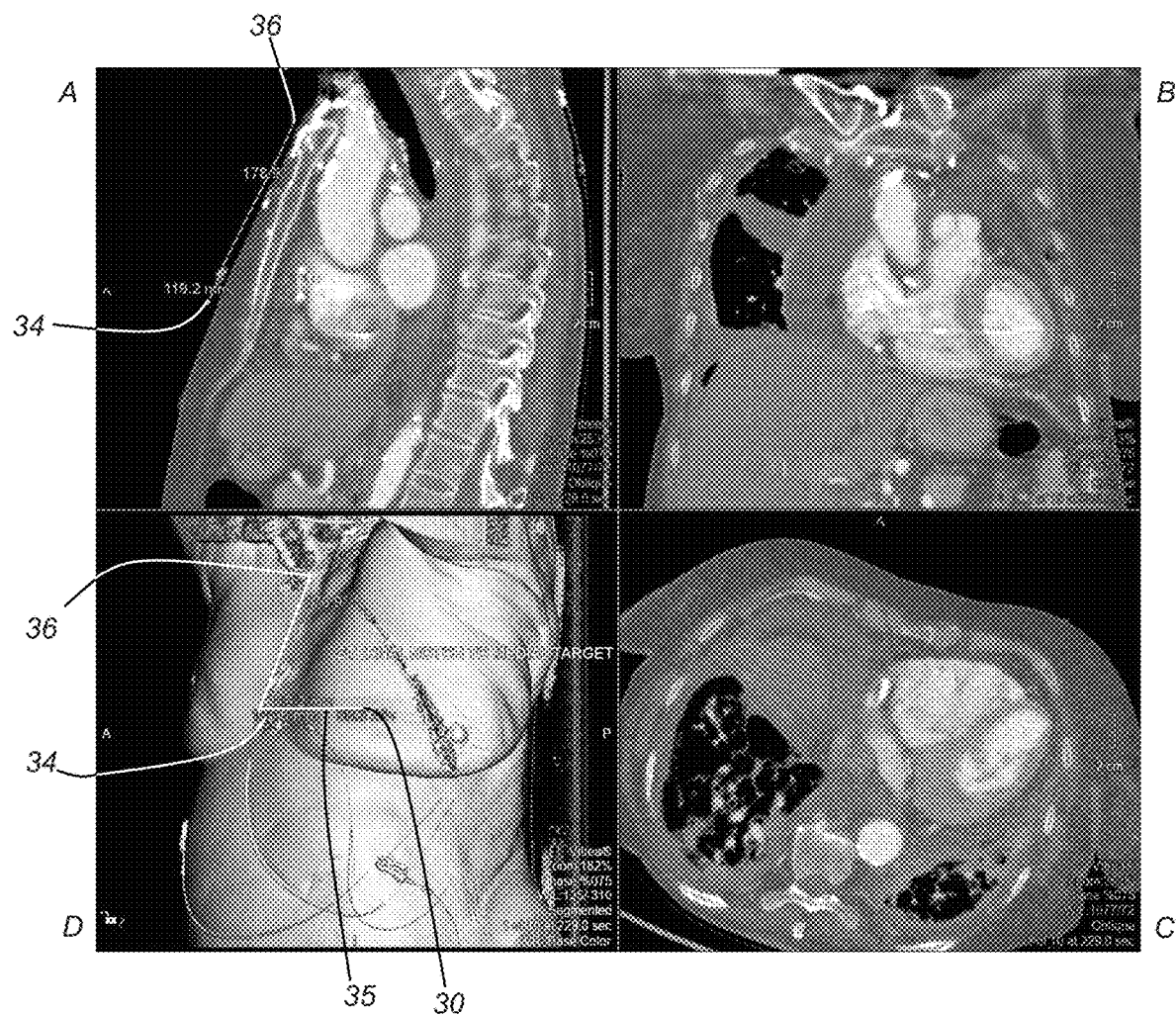
Figure 18:
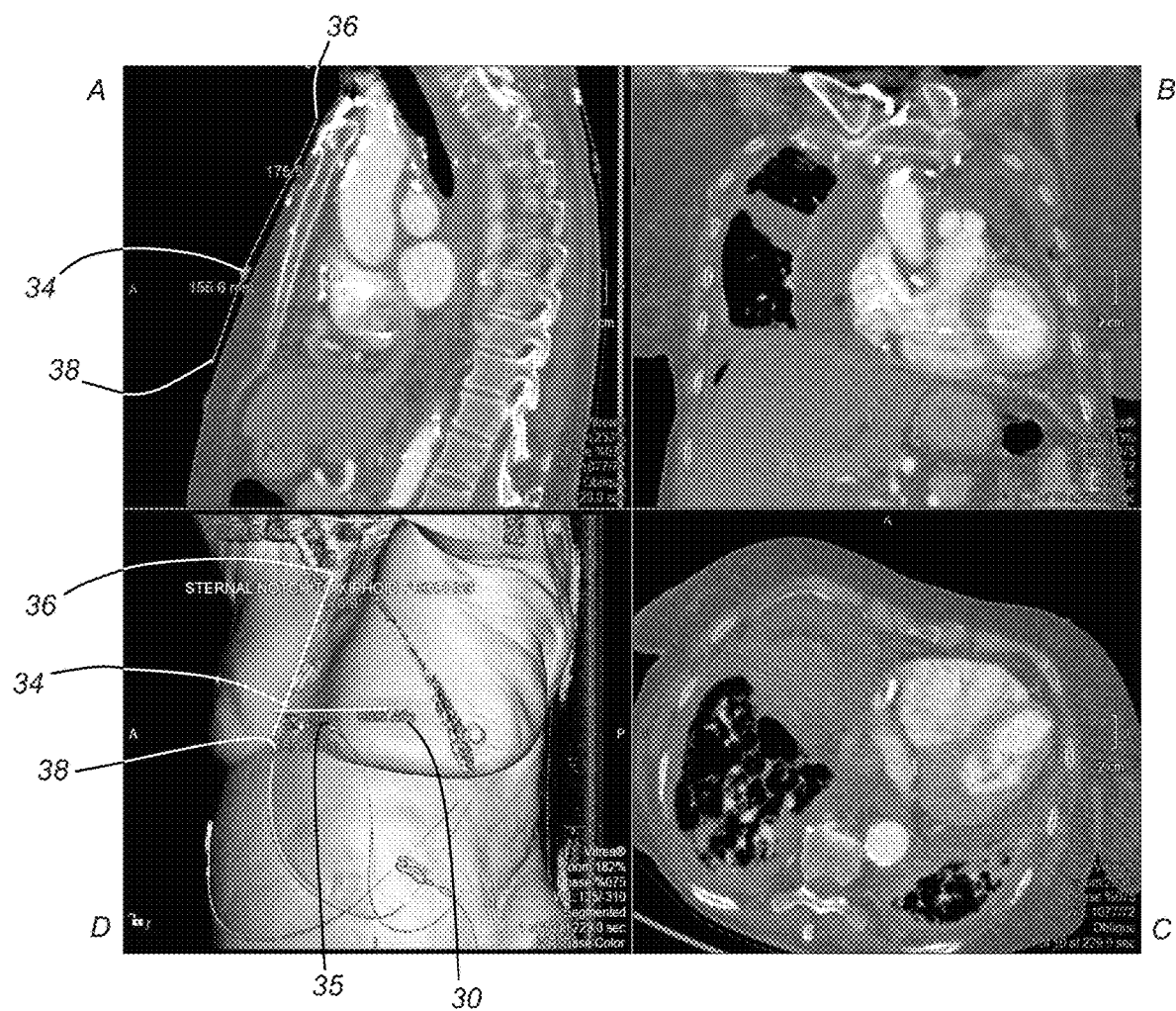

To designate the point of access on the patient, as opposed to merely representing it on a CT image, it is possible to relate the point of access to readily observable anatomical structures. In one embodiment, using the primary point of access image set 24, a 2D axial view is reproduced, as shown in FIG. 14. A distance 35 of the perimeter of the body to an area 34 at the mid-sternum can be measured. On a 3D model obtained from the primary point of access image set 24 (e.g., model D in FIG. 8), all of the layers of skin can be restored to view the patient's outer anatomy and to view the distance in a more anatomically reproducible form, as shown in FIG. 15. It is then possible to manually mark the point of access on the patient's body by measuring the distance from the patient's mid-sternum. This distance can also be corroborated with the patient's sternal notch. In an axial view from the primary point of access image set 24, the crosshairs can be moved back to perpendicular in order to angle the sagittal view. Then, on the sagittal view, as shown in FIG. 16, the distance from the sternal notch 36 to the mid-sternum point 34, which is aligned with the point of access 30, is measured. FIG. 17 further illustrates this distance. As shown in FIG. 18, a control measurement may be obtained by measuring the distance from the sternal notch 36 to the distal xiphoid process 38 along the skin's surface.

Figure 19:
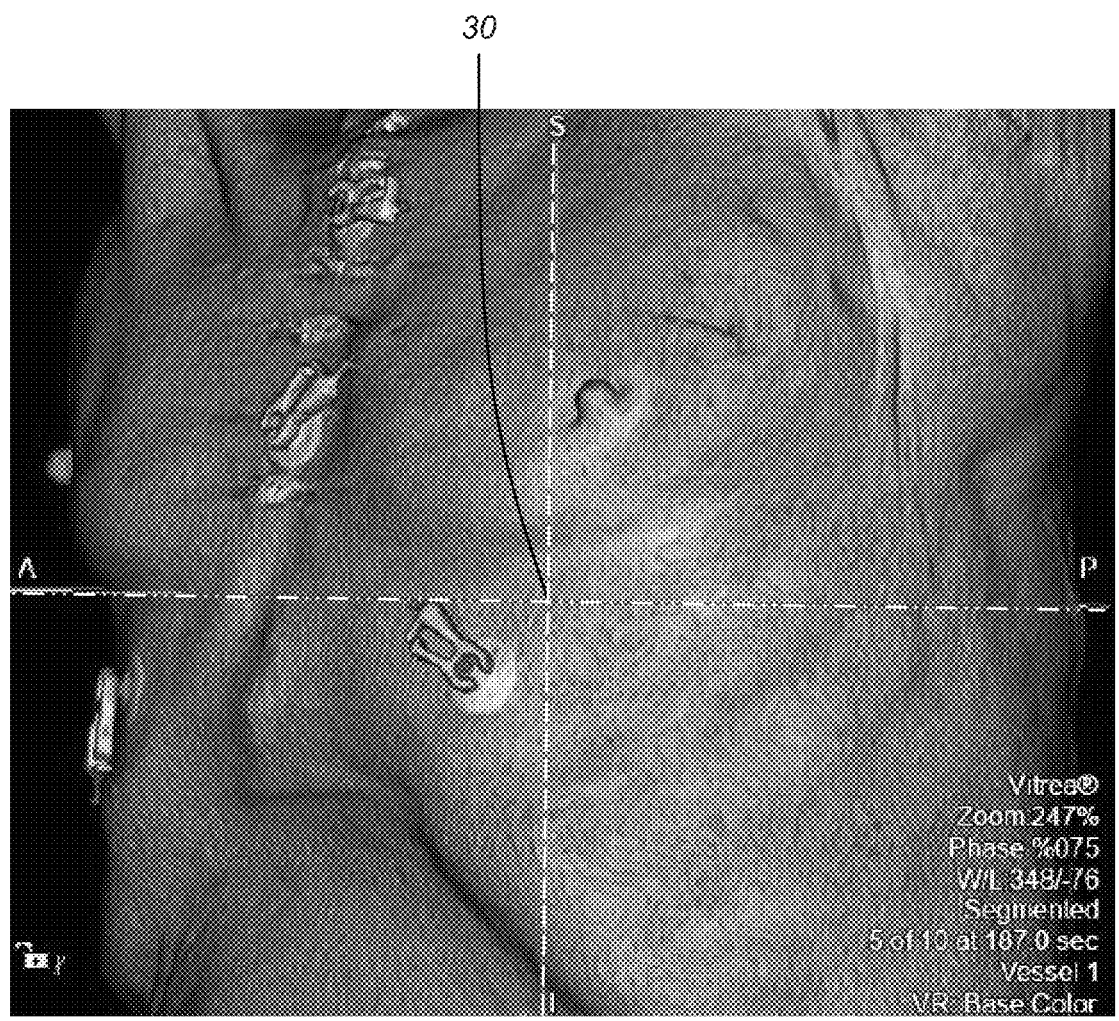
Figure 20:
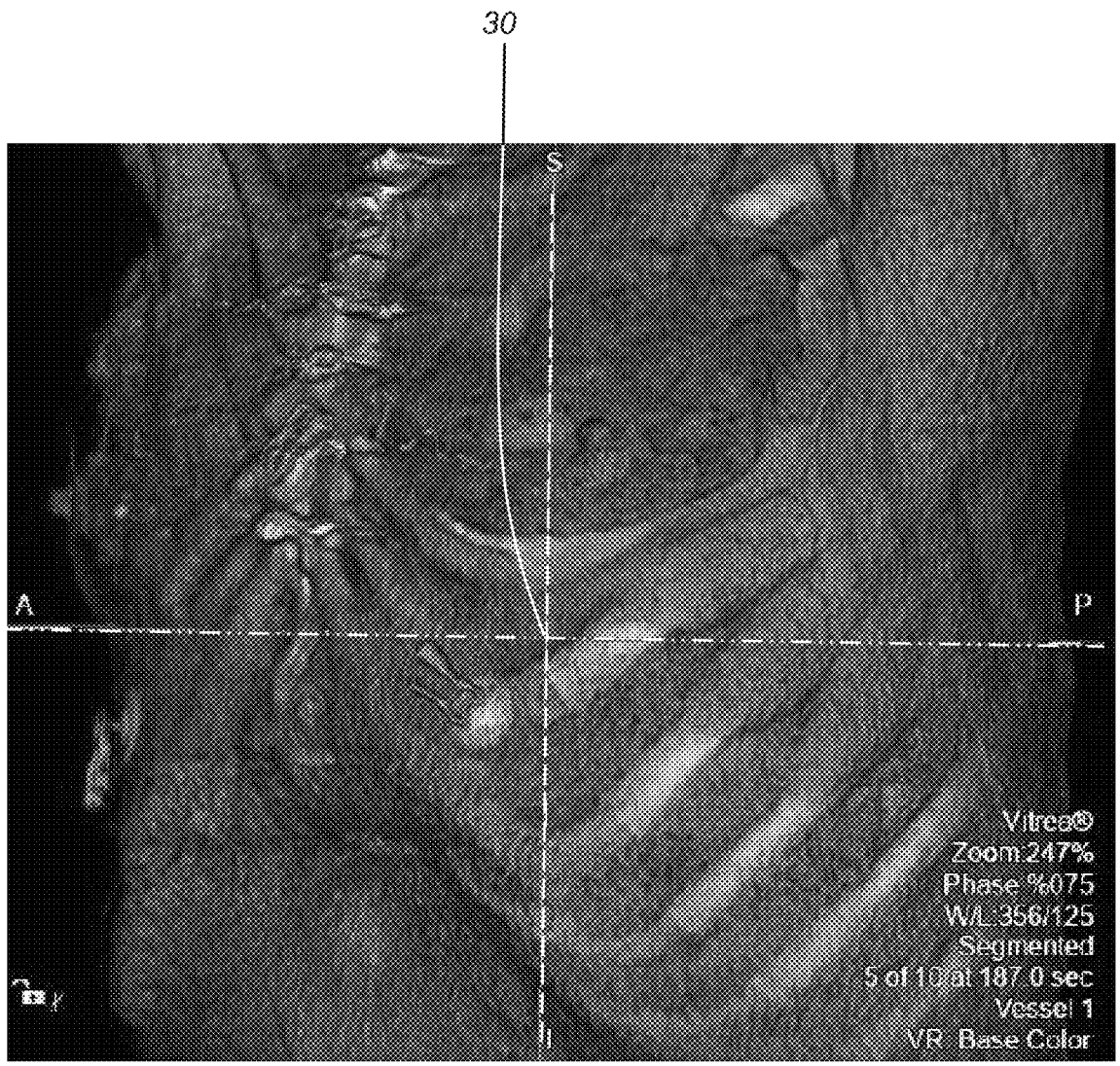
Figure 21:
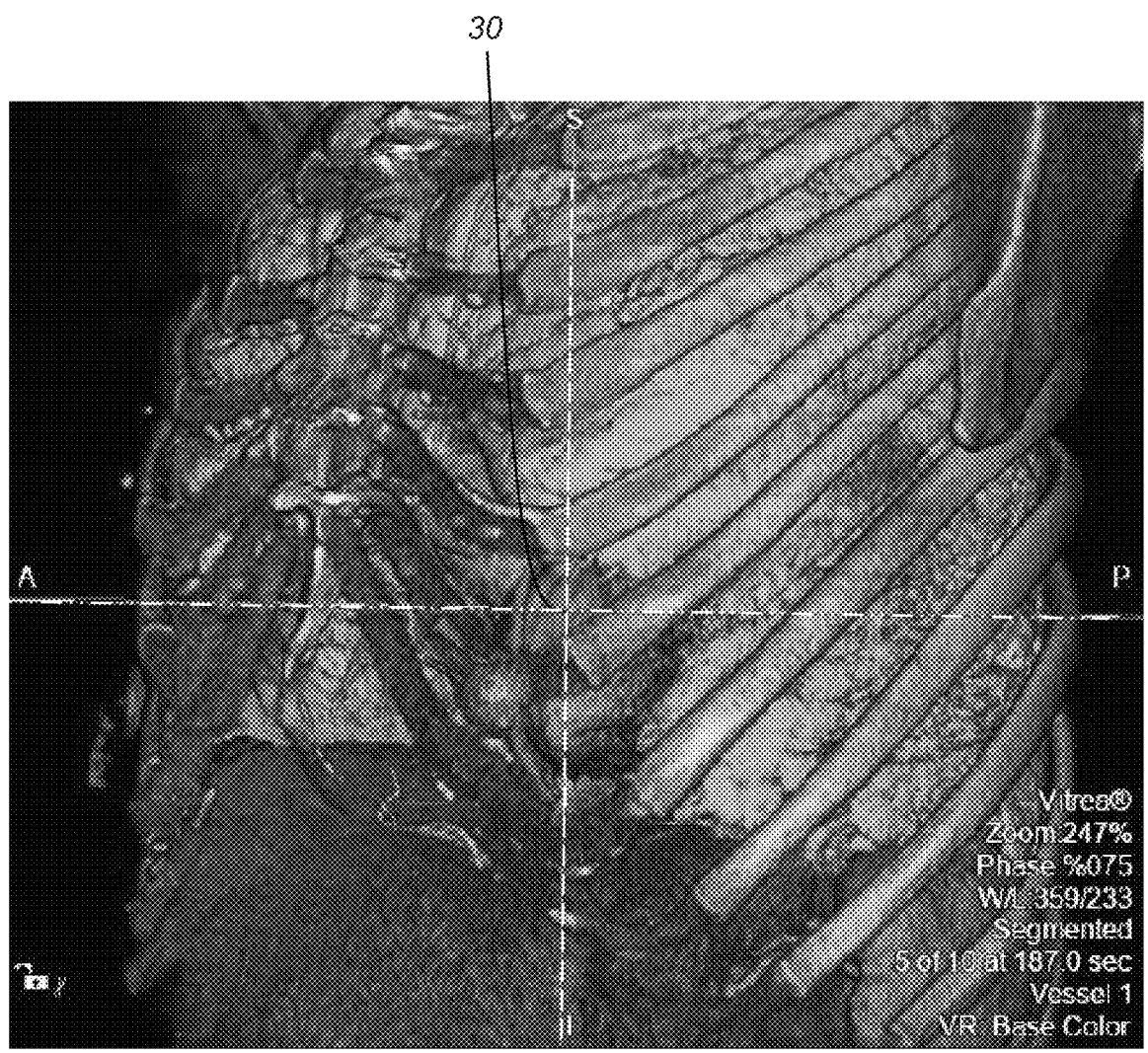
Figure 22:
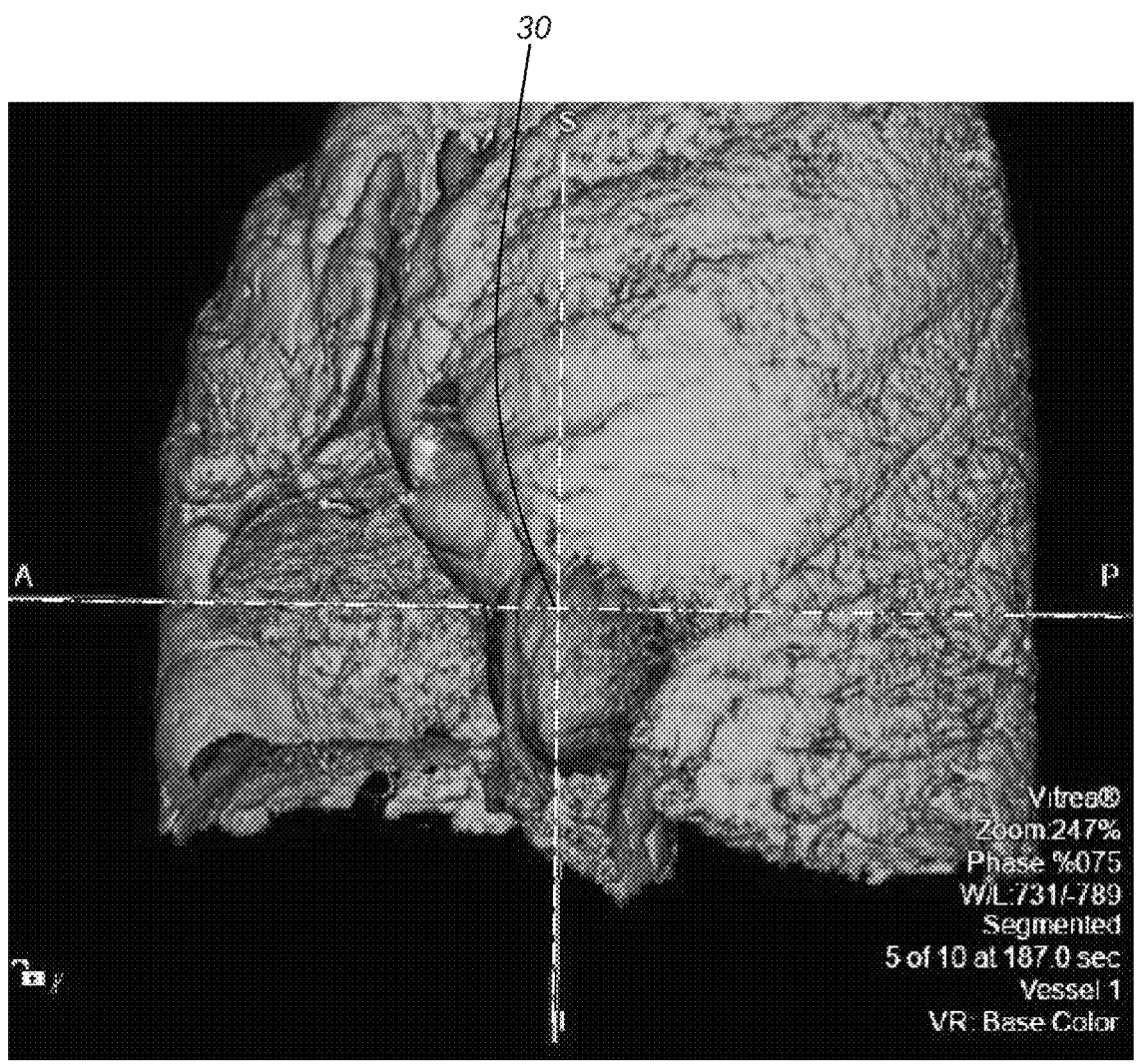
Figure 23:
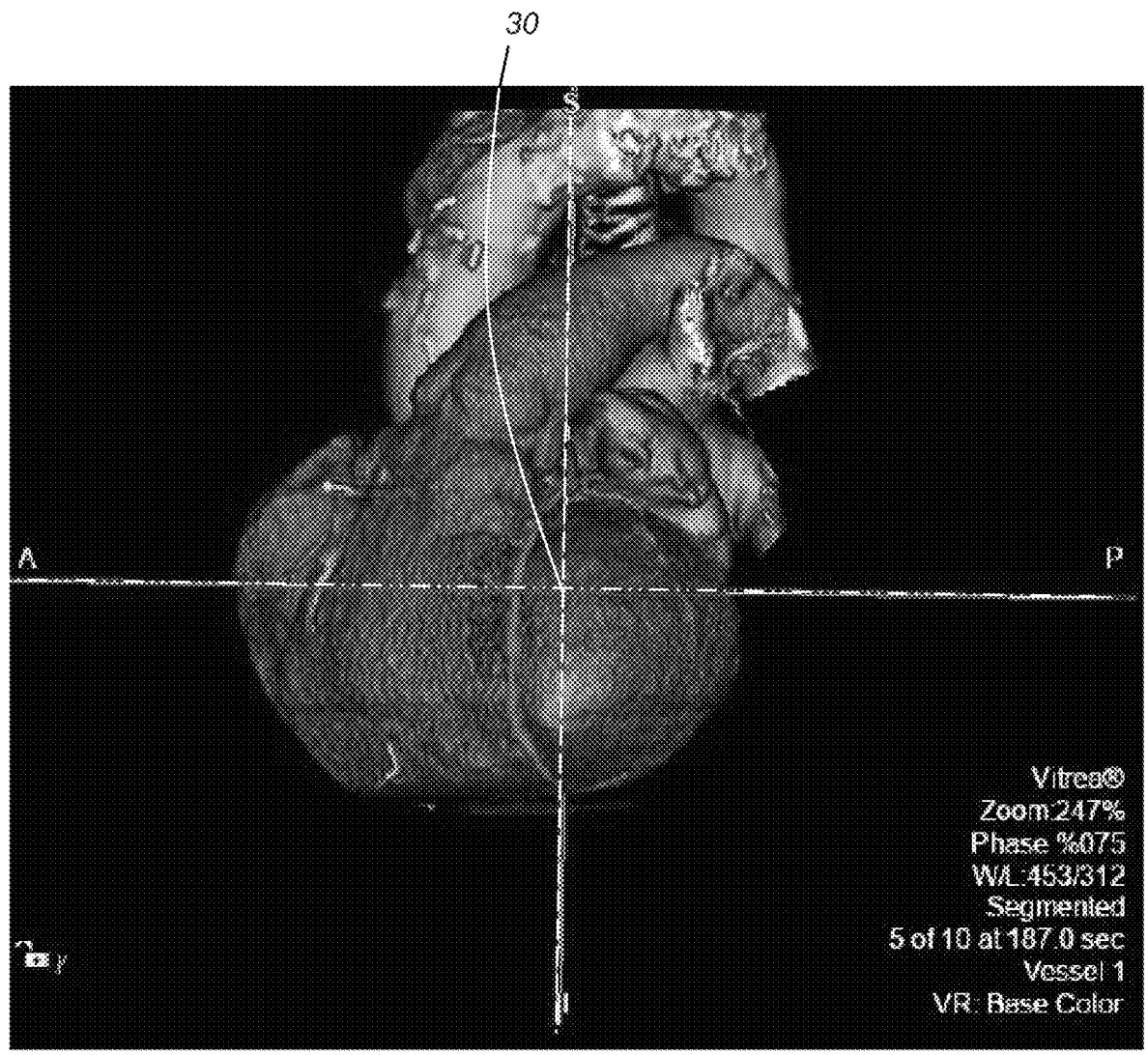
Figure 24:
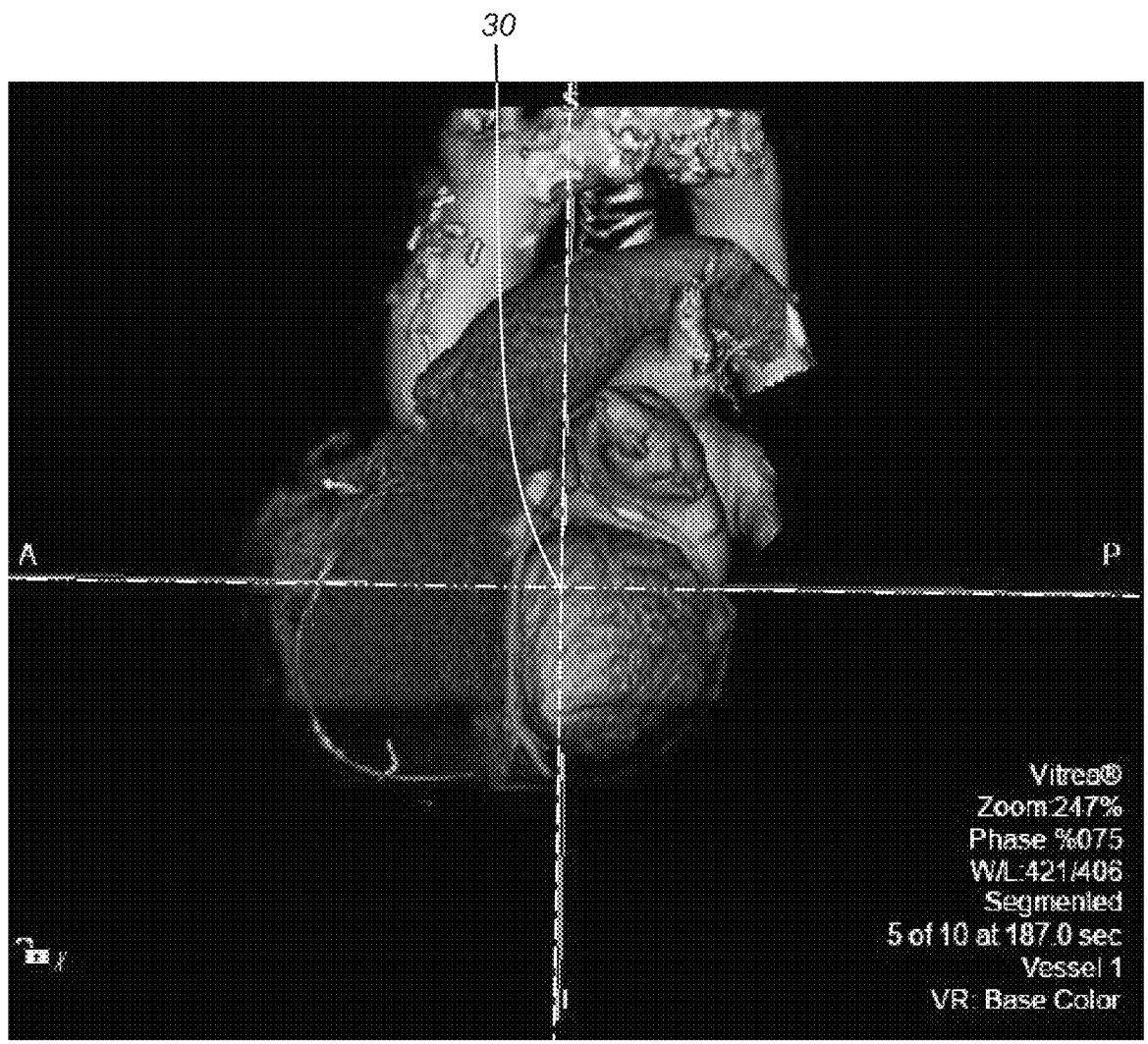
Figure 25:
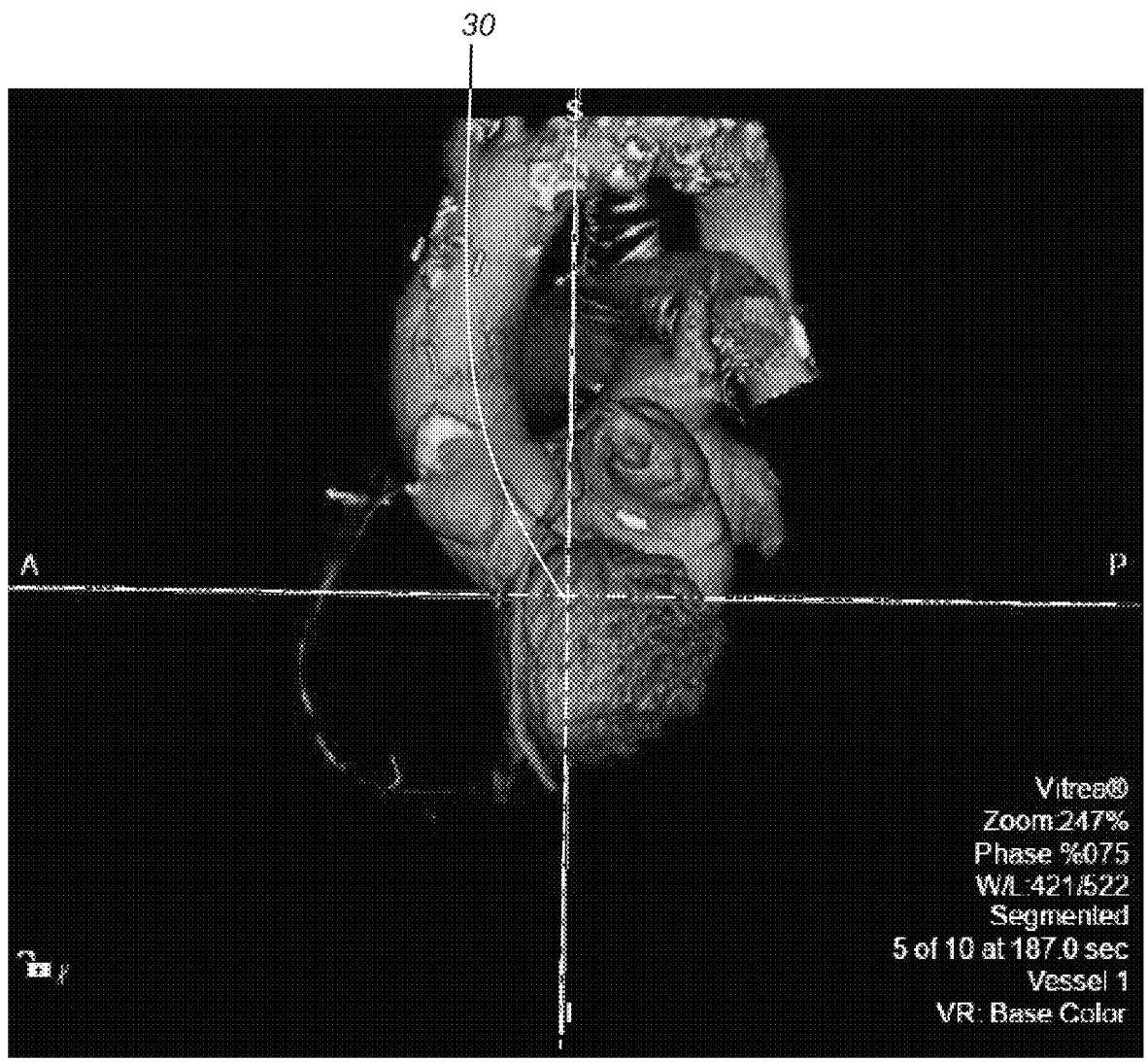
Figure 26:
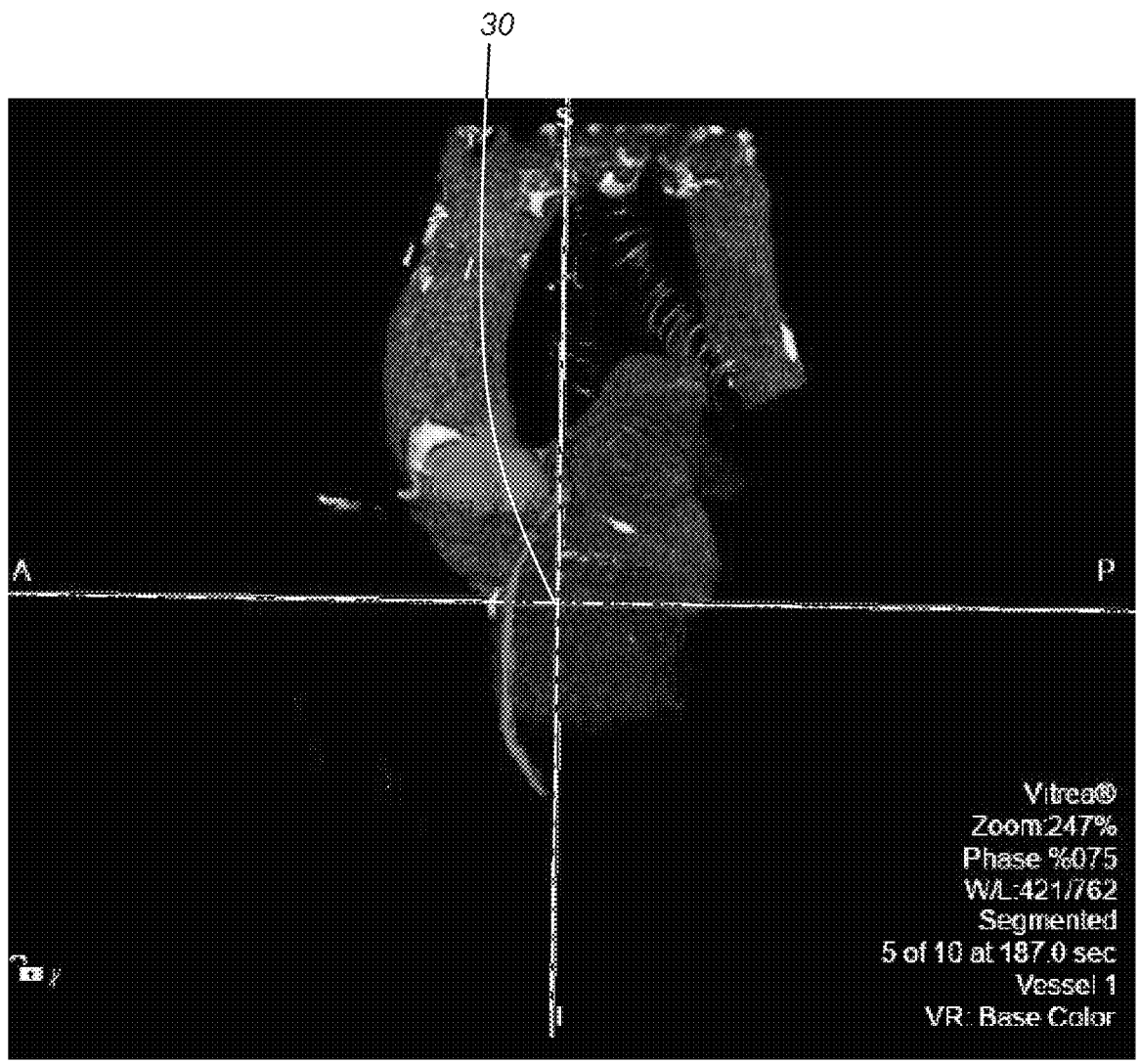
Figure 27:
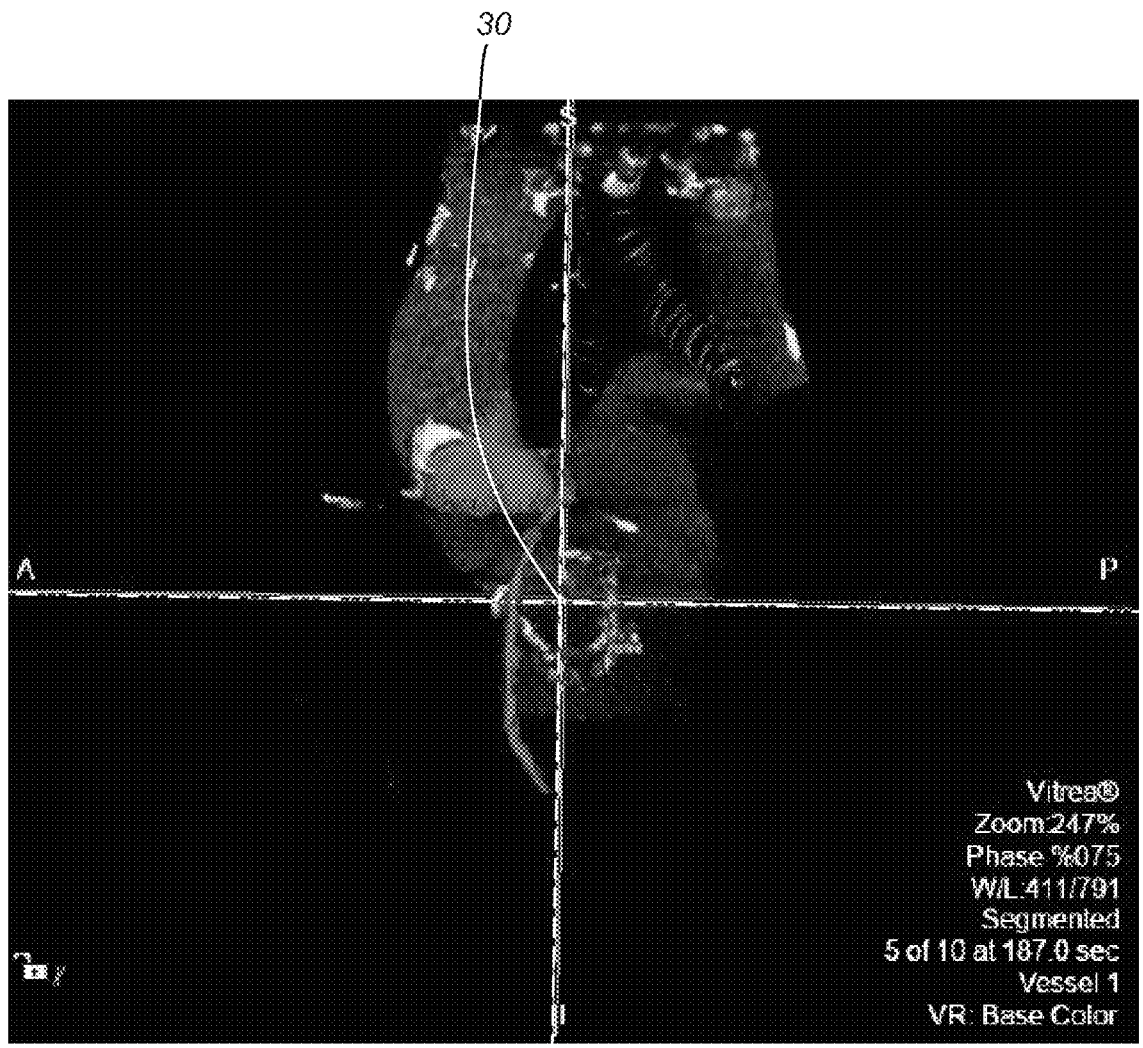

As a final verification for the point of access determination, it is possible to show the point of access on a model of the body that includes a representation of the surface of the patient's body, and then intervening anatomical structures may be removed by, for example, a physician using a user interface device such as that or those described below, layer-by-layer until the anatomical structure of interest is in view. The layer-by-layer removal of intervening anatomical structures may also be performed automatically by a system, such as the system 200 described below, and played in movie form for a physician, for example. FIG. 19 shows the point of access 30 on a 3D coronal projection showing the surface of the skin. FIG. 20 is the same representation as FIG. 19 but with the outer skin layer removed. FIG. 21 is the same representation that then shows the point of access 30 with the muscles removed. FIG. 22 is the same representation that then shows the point of access 30 with the ribs removed. FIG. 23 is the same representation that shows the point of access 30 with the lungs removed. FIGS. 24-26 are the same representations showing the point of access 30 with various cardiac structures removed until the blood volume is shown. Finally, FIG. 27 shows the point of access 30 aligned with the anatomical structure of interest. This layer-by-layer process can be repeated at a different C-arm angle to show optimal C-arm viewing of the patient's anatomy while the procedure is occurring. It is also possible to make a cine loop showing all of the phases of the cardiac cycle. For the cine loop, it is preferable that the anterior sternum is removed to provide a better view of the anatomy.

Optional step 112 of the method estimates the volume of the anatomical structure of interest. According to one embodiment, the volume is estimated based on the fluid capacity of the structure. For example, internal blood volume may be used to estimate the anatomical structure volume. When a patient is injected with an iodinated contrast in preparation for the CT procedure, the blood shows as bright areas within the blood vessels. Utilizing blood volume dimensions such as circumference and area can help to predict the degree of gaps or paravalvular leakage that will appear when reconciling the anatomical structure size and the implant size, as described in more detail with relation to step 114. In accordance with one embodiment, the fluid volume is estimated using a modified Simpson's calculation. The Simpson method is also known as the method of discs because it integrates volume by fitting numerous elliptical discs into the hollow anatomical structure and summing up their volume. The volume of each disc is determined by the diameter of the disc and its height, and may be calculated according to the following equation:

$$\text{Volume} = (A1 + A2 + \ldots + An) * h;$$

where "h" represents the height of each disc, which is calculated as a fraction of the long axis of the anatomical structure, and "A" represents the area which can be determined based on the particularly shaped disc that will fit at that particular point. For example, if the disc is generally circular, the area is a function of the disc's diameter, D:

$$A = \pi * (D/2)^2;$$

however, it is possible to use other shapes to determine the area, depending on the best fit in a particular location. In one embodiment, the calculations are carried out more than once in different views. For example, it may be desirable to size the volume of a blood vessel in both a two chamber view and a four chamber view. The cross-sectional area of the disc is then based on the two diameters obtained from the orthogonal views. It should also be noted that the Simpson's method described above can also be performed using an ultrasound image.

Figure 28:
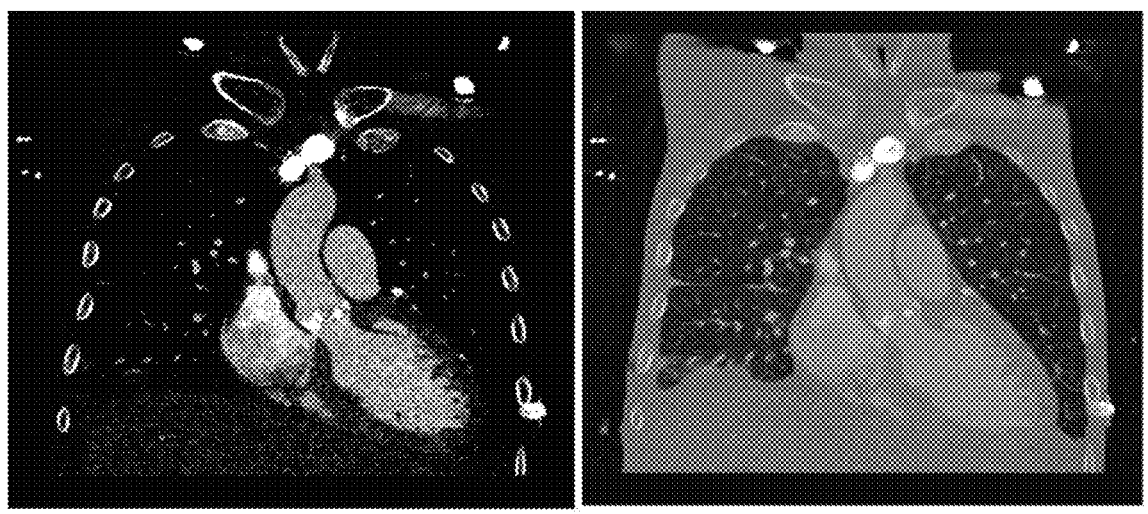
Figure 29:
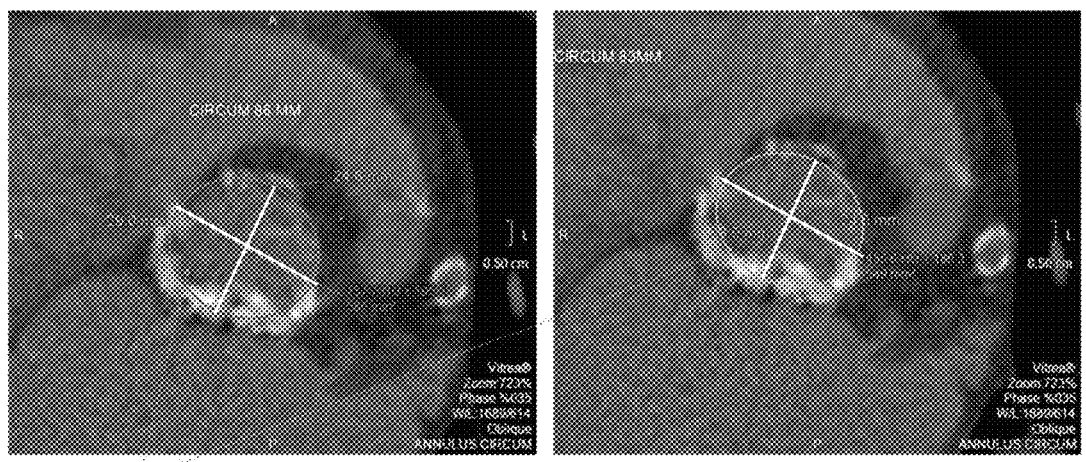

One aspect of estimating the anatomical structure volume may take into account mineral deposits on the interior walls of a hollow anatomical structure. In one particular embodiment, the amount of calcium and its impact on the anatomical structure volume is determined. Heavily calcified heart valves and vessels can create a "blooming artifact" on a CT image. The blooming artifact is a zone of haziness pictured around calcium deposits identified by the CT scanner, which makes it difficult to determine the demarcation point between the vessel wall and the calcium deposit. FIG. 28 shows a heavily calcified aortic annulus on the left, and the right shows a "windowed down" version where the brightness of the calcium on the screen is decreased. This shows more of a density gradient across the calcium and minimizes the appearance of the calcium. FIG. 29 represents a beam hardening artifact which occurs within a heavily calcified aortic annulus. A beam hardening artifact may be represented as a "gap" in the image that occurs from the x-ray beam encountering a material with a high density that disperses the x-ray radiation, creating an artificial "dropout" effect. The arrows indicate the beam hardening artifact which causes an obstruction in accurately measuring the area because it is difficult to determine whether there is a true cut off of the annulus, or whether it is merely a beam hardening artifact that appears as a black spotted area. The variable measurements between the two images in FIG. 29 would lead to one valve size given one set of measurements, and another valve size given another set of measurements. One possible way to quantify the calcium deposit density, size, and volume is through 3D modeling estimation. To quantify the calcium deposit and tissue differentiation needed for an adequate 3D printed model from CT scan data, it is possible to use current durometers available for 3D printers. Each durometer (e.g., ink jet for a 3D printer) is typically calibrated to a certain density. By mixing known densities of calibrated durometers into aliquots in a premade tray for scanning, it is possible to scan the variously calibrated durometers using the CT scanner. Acquired images can then reflect the different hounsfield units or density uptake of the durometers on the acquired CT image. Data already exists on the proposed densities and hounsfield units for skin, tissue, blood, water, bone, and other tissue differentiations. By analyzing the scan from the durometer, it is possible to know what density formula is representative of the corresponding hounsfield unit of the particular anatomical body part (e.g., calcium). This may allow for a more accurate representation of the density of the anatomical structure of interest, and a more accurate assessment of the peri-operative and transcatheter needs for catheter sizing, such as the devices needed for entry into the body and device implantation specifics. Validating the degree of calcium present on a raw CT data acquisition in reference to known calcium models in vivo and ex vivo allows for improvement in the qualification and quantification of dimensional analysis of anatomical structure sizing.

Figure 30:
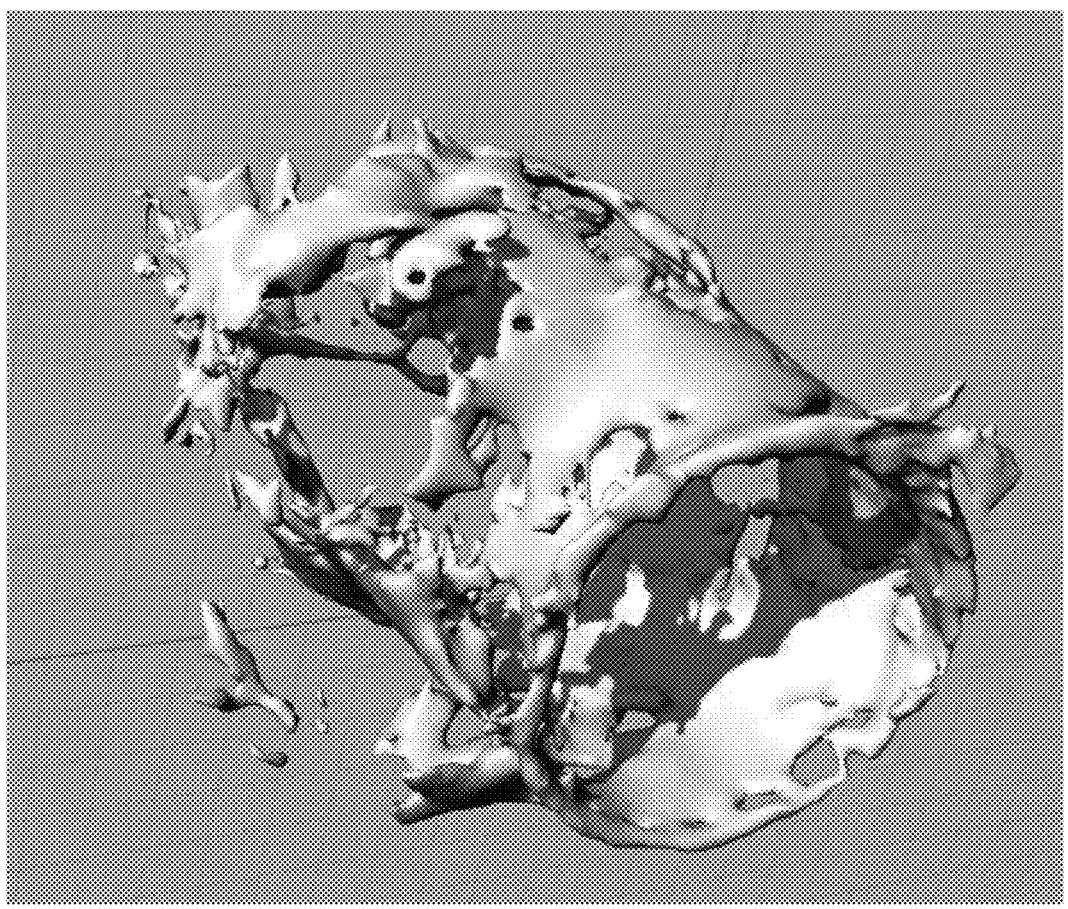
FIG. 30 is a 3D rendering of a vessel structure derived from estimated blood volume.
Figure 31:
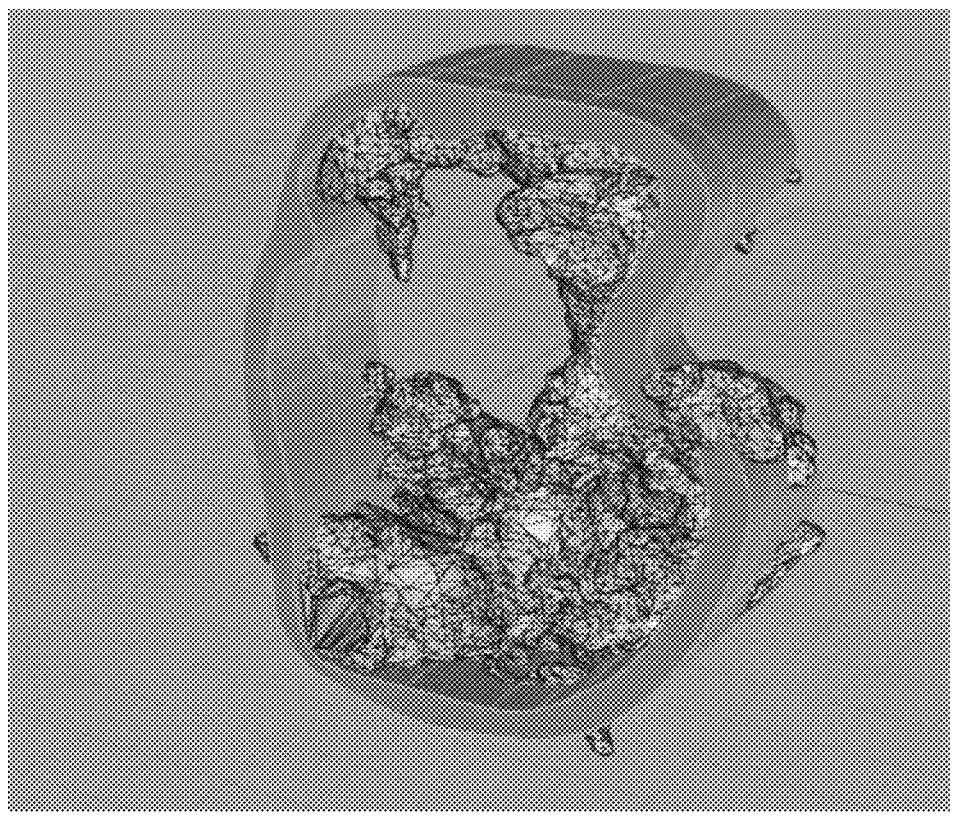
FIG. 31 is a 3D rendering of a mitral valve annulus with calcification.

In accordance with a particular embodiment, the blood volume, calcium deposits, or both the blood volume and calcium deposits are used to develop a 3D model, for example a 3D computer-aided design (CAD) model, of the anatomical structure of interest or at least a portion of the anatomical structure of interest. The 3D CAD model is constructed from CT data that is imported into an STL file. An interfacing bridging software, such as programs developed by Mimics, can take the raw CT data (i.e., the hounsfield units) and use the changes in shade, which are indicative of changes in tissue and/or fluid composition, to develop certain shading thresholds that can be used to build a 3D model. It is possible to sculpt the image by either paring down the CT data prior to importing it into an STL file, or it may be possible to pare down the 3D CAD image after it has been created. FIG. 30 shows a 3D CAD model of a hollow cardiac structure developed based on internal blood volume and modeling/showing the interior surface of the structure. FIG. 31 shows a 3D CAD model of a mitral annulus showing areas of heavy calcification. A 3D CAD model can also be used to print a 3D model of the anatomical structure of interest or a portion of the anatomical structure of interest, which may then be used for a variety of purposes, some of which are described below.

Figure 32A:
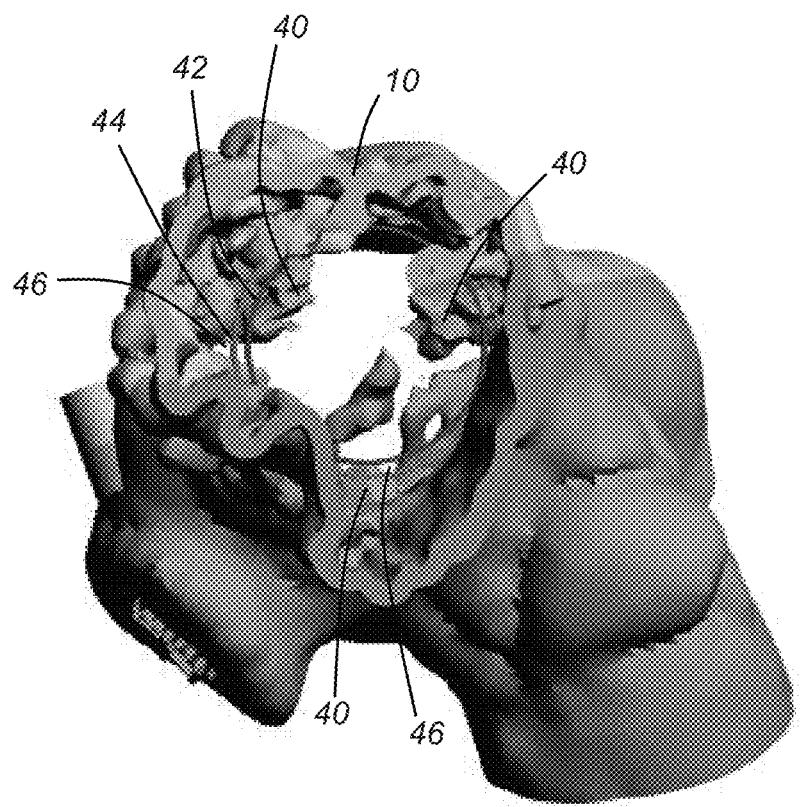
FIGS. 32A and 32B are 3D renderings of a mitral valve annulus depicting the sizes of possible replacement mitral valves.
Figure 32B:
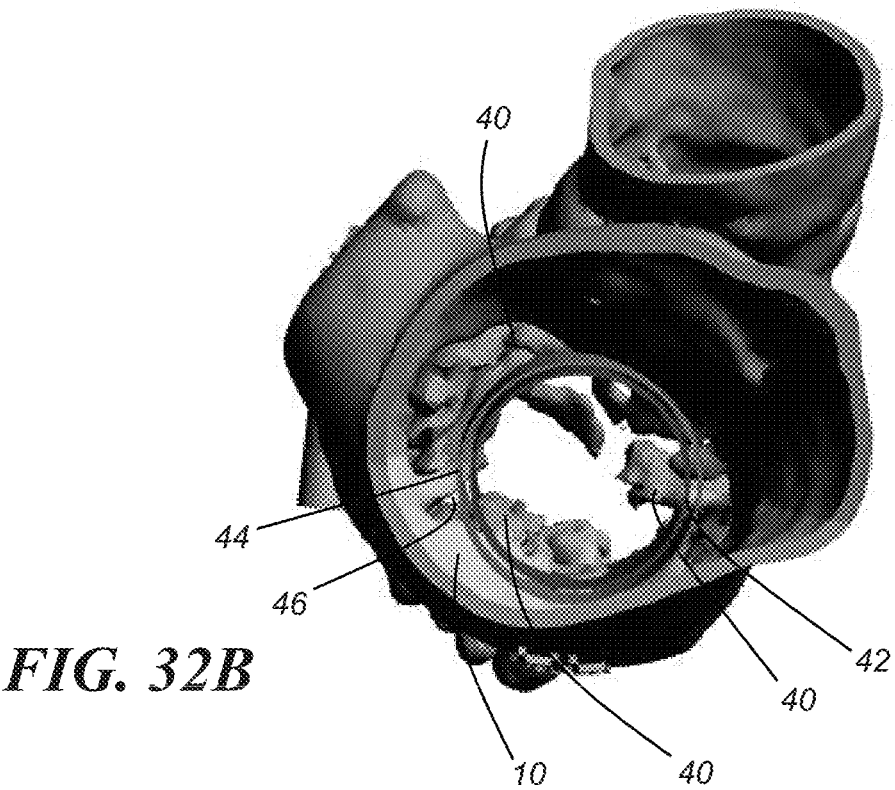

Step 114 involves reconciling the size of the anatomical structure of interest and the size of an implant. The anatomical structure size may be based on one or more of the measurements attained in step 108 of the method, the volume estimated in step 112 of the method, or it may be based on one or more of the measurements attained in step 108 in combination with the volume estimated in step 112. In an embodiment, the anatomical structure size is modeled using a 3D CAD model, as described above and depicted in FIGS. 32A and 32B which show opposite views of the mitral valve 10. Included are areas of calcification 40 and 3D models of two potential implants, for example, 3D CAD models of two potential implants, or in this particular embodiment, prosthetic valves 42, 44. One or more models of implants may be imported into the 3D model of the anatomical structure and may be appropriately positioned by the physician using, for example, one or more of the user interface devices described below, to assess issues such as the fit and suitability of one or more potential implants. For example, this modeling allows for the analysis of gaps 46 which are indicative of areas of potential leakage. Calcium at the mitral leaflet tips and the mitral annulus may provide varying amounts of support to the prosthetic valve. Moreover, modeling provides a way to analyze an ideal location to anchor the implant, for example either deeper within or higher above the calcification.

Figure 33A:
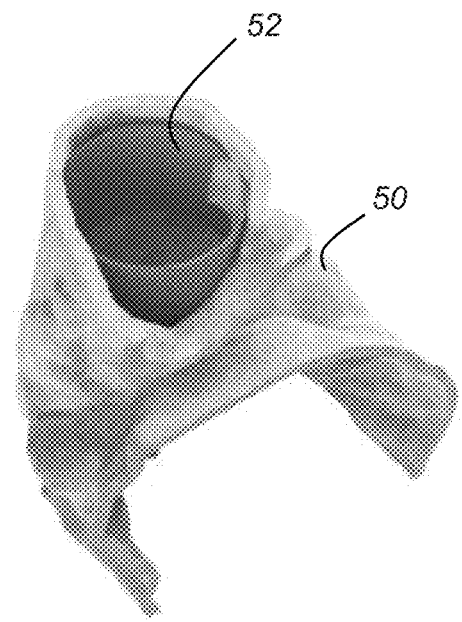
FIGS. 33A-33C show different views of a 3D printed model of the right atrium inferior vena cava junction having an implant disposed therein.
Figure 33B:
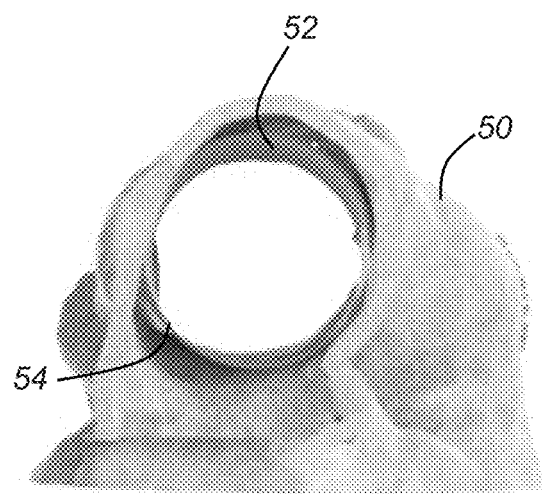
Figure 33C:
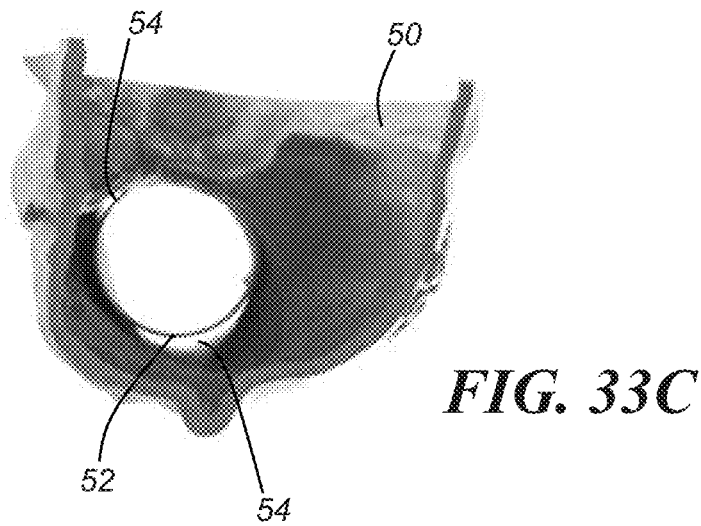

In another embodiment, the anatomical structure size is modeled using a 3D printed representation of the structure itself, as shown in the various views depicted in FIGS. 33A-33C. FIGS. 33A-33C show a 3D printed model of a right atrium inferior vena cava junction 50 with a prosthetic valve 52. Given the funnel shaped anatomy of the dilated inferior vena cava, it is possible to print the patient's right atrium extending into the inferior vena cava, and in one particular case, ending just above the first hepatic vein. Areas of potential leakage 54 provide a physician guidance when choosing the most appropriate valve. According to another embodiment, both the 3D CAD model and the 3D printed model allow for analysis of aortic leaflet length and leaflet motion with respect to a potential risk of coronary ostium obstruction from valve deployment, or leaflet obstruction of coronary ostia in prosthetic valves with higher, more prominent heights and statures. It should also be recognized that 3D modeling and printing work particularly well with the left atrial appendage.

Figure 34:
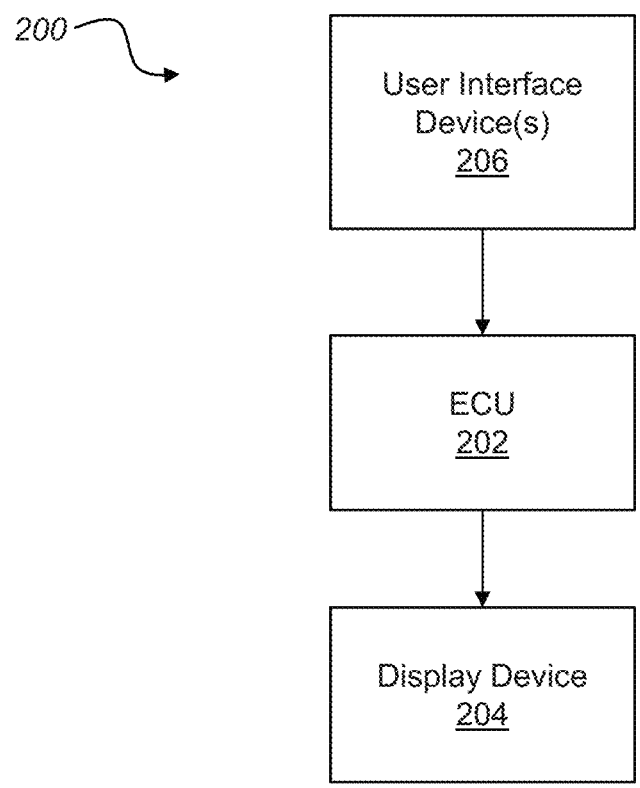
FIG. 34 is a schematic and block diagram of an illustrative embodiment of a system for performing the method illustrated in FIG. 4.

In addition to the methodology described above, another aspect of the disclosure includes a system or apparatus for performing some or all of the steps of method 100 described above. With reference to FIG. 34, a system 200 may comprise, among potentially other components, an electronic control unit (ECU) 202, a display device 204, and one or more user interface devices 206.

The ECU 202 may comprise one or more electronic processing units and one or more electronic memory devices, as well as, for example, input/output (I/O) devices and/or other known components. In another embodiment, rather than, or in addition to, the ECU 202 comprising a memory device, the system 200 may include one or more memory devices that are separate and distinct from the ECU 202 (and the processing unit(s) thereof, in particular) but that is/are accessible thereby.

The processing unit of the ECU 202 may include any type of suitable electronic processor (e.g., a programmable microprocessor or microcontroller, an application specific integrated circuit (ASIC), etc.) that is configured to execute appropriate programming instructions for software, firmware, programs, algorithms, scripts, etc., to perform various functions, such as, for example and without limitation, one or more steps of the methodologies described herein.

The memory device, whether part of the ECU 202 or separate and distinct therefrom, may include any type of suitable electronic memory means and may store a variety of data and information. This includes, for example, software, firmware, programs, algorithms, scripts, and other electronic instructions that, for example, are required to perform or cause to be performed one or more of the functions described elsewhere herein (e.g., that are used (e.g., executed) by ECU 202 to perform various functions described herein). Alternatively, rather than all of the aforementioned information/data being stored in a single memory device, in an embodiment, multiple suitable memory devices may be provided. These are, of course, only some of the possible arrangements, functions and capabilities of ECU 202, as others are certainly possible. In any event, in at least some embodiments, the memory device may comprise a computer program product, or software, that may comprise or include a non-transitory, computer-readable storage medium. This storage medium may have instructions stored thereon, which may be used to program a computer system (or other electronic devices, for example, the ECU 202) to implement the control of some or all of the functionality described herein. A computer-readable storage medium may include any mechanism for storing information in a form (e.g., software, processing application) readable by a machine (e.g., a computer, processing unit, etc.). The computer-readable storage medium may include, but is not limited to, magnetic storage medium (e.g., floppy diskette); optical storage medium (e.g., CD-ROM); magneto optical storage medium; read only memory (ROM); random access memory (RAM); erasable programmable memory (e.g., EPROM and EEPROM); flash memory; or electrical, or other types of medium suitable for storing program instructions. In addition, program instructions may be communicated using optical, acoustical, or other form of propagated signal (e.g., carrier waves, infrared signals, digital signals, or other types of signals or mediums).

The display device 204 may comprise any number of display devices known in the art, for example and without limitation, liquid crystal display (LCD), cathode ray tube (CRT), plasma, or light emitting diode (LED) monitors or displays. The display device 204 is electrically connected or coupled to the ECU 202, and is configured to be controlled by the ECU 202 such that images or models of anatomical structures generated or acquired by the ECU 202, including those described above with respect to method 100, may be displayed thereon and may be used for the purposes described herein. Additionally, in an embodiment wherein the ECU 202 may be configured to generate an interactive graphical user interface (GUI) that allows, for example, a physician to manipulate images or models displayed on the display device (e.g., removing layers of a model, rotating models, etc.), facilitate the taking of measurements, etc., the display device 204 may also display such a GUI. In any event, the display device 204 is configured to receive electrical signals from the ECU 202 and to display content represented by the received signals which may be viewed by, for example, a physician.

The user interface device(s) 206 may comprise any number of suitable devices known in the art. For example, and without limitation, the user input device(s) 206 may comprise one or a combination of a touch screen (e.g., LCD touch screen), a keypad, a keyboard, a computer mouse or roller ball, and/or a joystick, to cite a few possibilities. In certain implementations, the display device 204 and user input device 206 may be combined together into a single device. Regardless of the particular form the user interface device(s) take, the user input device(s) 206 may be electrically connected or coupled (e.g., via wired or wireless connections) to the ECU 202, and are configured to facilitate a measure of communication between a user (e.g., physician) and the system 200, and the ECU 202 thereof, in particular. More particularly, the user interface device(s) 206 may allow a physician to manipulate images or models displayed on the display device 204 (e.g., rotate images or models, strip away or add layers to a model or image, move models relative to each other, etc.), to take desired measurements of anatomical structures represented by or in the images or models displayed on the display device 204, etc.

While certain components of the system 200 have been described above, it will be appreciated that in some implementations, the system 200 may include more or fewer components than are included in the arrangement described above. Accordingly, the present disclosure is not intended to be limited to any particular implementation(s) or arrangement(s) of the system 200.

Figure 35:
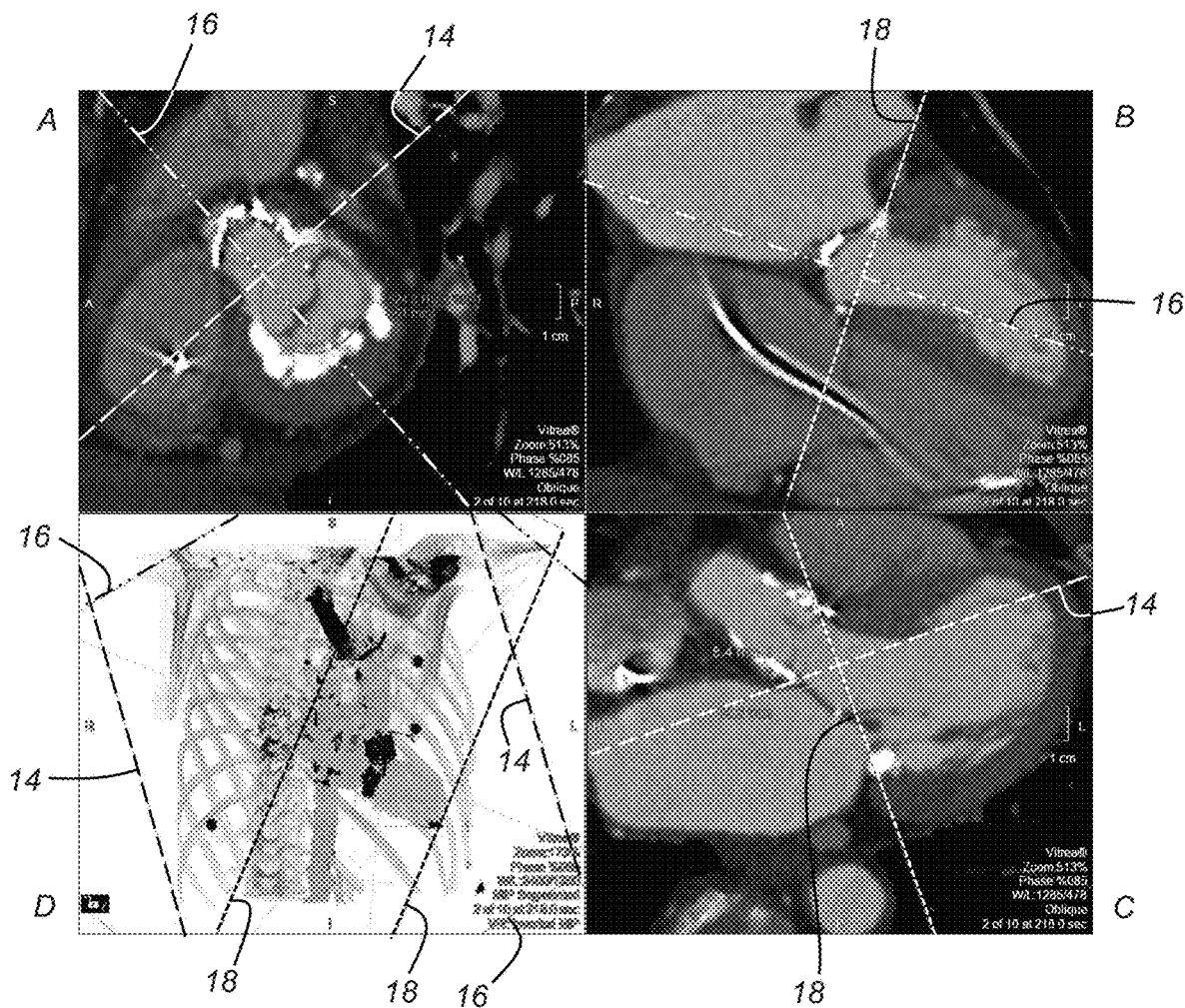
FIG. 35 is an image set comprising images of a mitral valve acquired from an imaging system.
Figure 36:
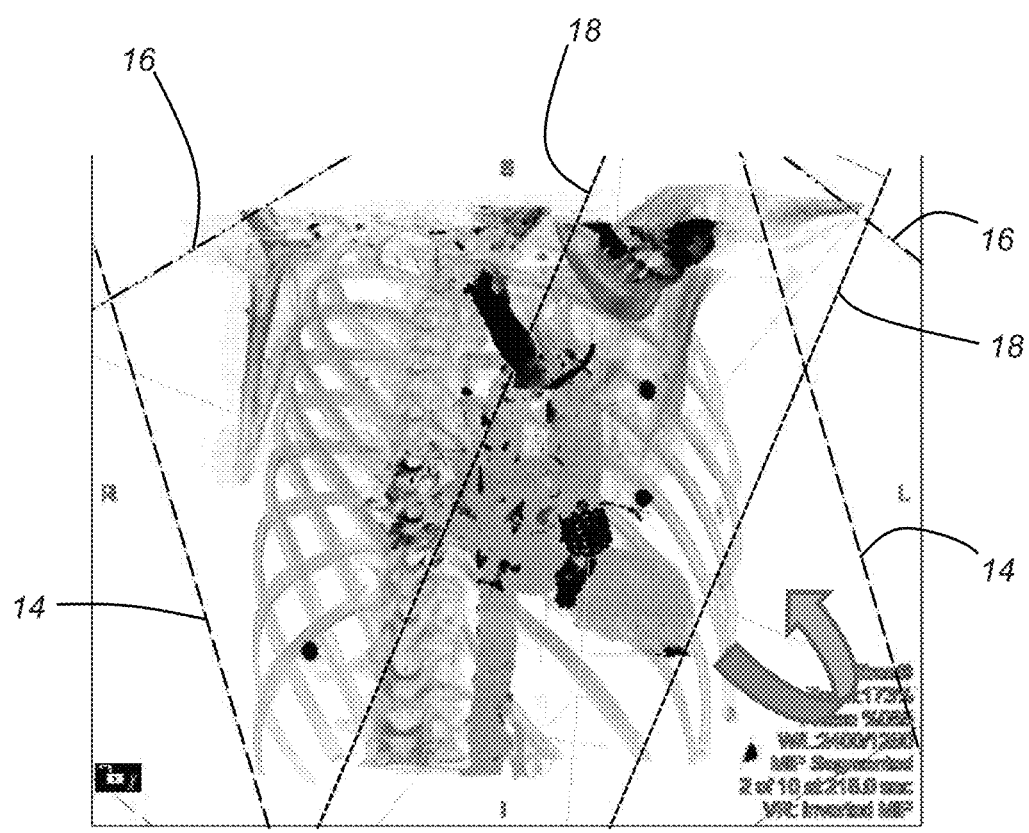
FIG. 36 is an enlarged view of the 3D image D of FIG. 35.
Figure 37:
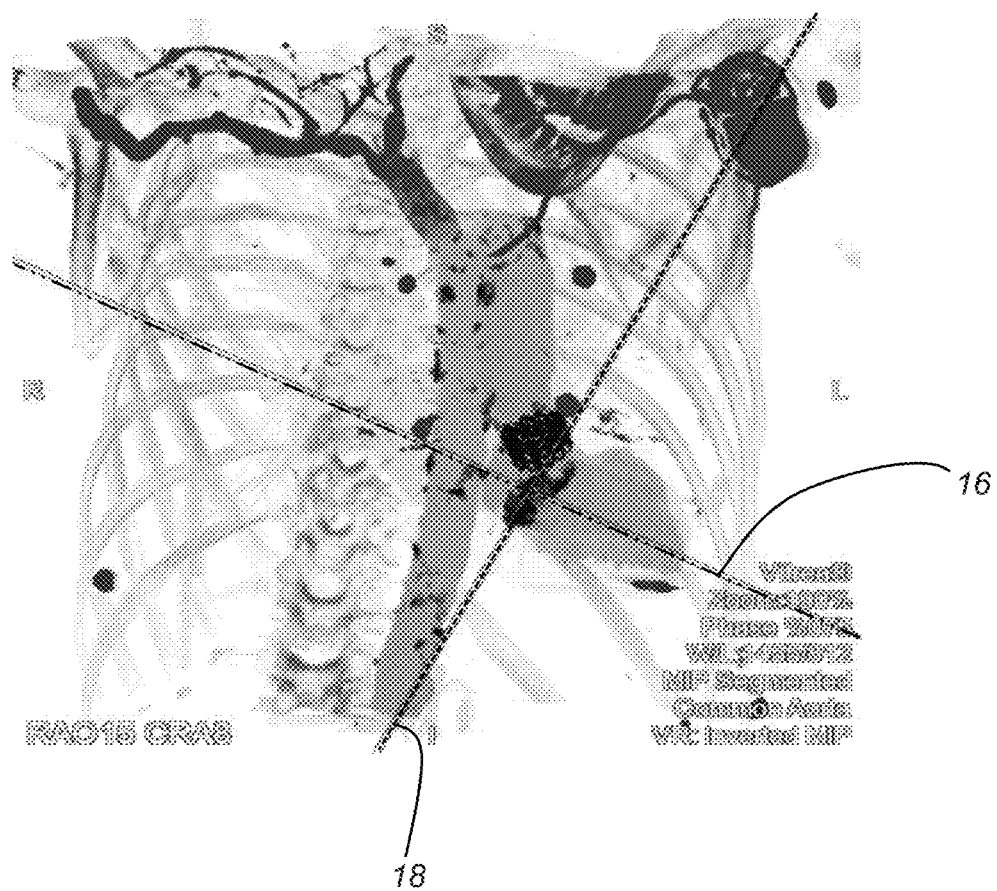
FIG. 37 is the 3D image D of FIGS. 35 and 36 shown from a different perspective.

FIGS. 35 and 36 can be used to simulate the cardiac catheterization fluoroscopic projection, which may be done for purposes of steps 108 and steps 110 above. A maximum intensity projection (MIP), which displays the brightest voxel of a CT image, can be helpful to visualize vasculature. With reference to the mitral annulus example, MIP inversion may be applied, and a 3D image may be built that includes in the field of view: the ribs, spine, left atrium, left ventricle, aorta, the aortic valve, and the first hepatic vein, for example. This 3D image can then be projected in a black-white radiograph simulation. The original perspective of the mitral annular sizing plane can be restored into the 3D MIP inverted image and the spinous processes should be marked in the coronal view and the sagittal view, which allows for a physical demarcation for the trajectory of the C-arm transapical angulation. To determine C-arm angles, as shown in FIG. 35, the mitral valve plane image may be restored. All plane indicators should be applied to the 3D image D. Then, in the 3D image D, which is shown enlarged in FIG. 36, it is possible to rotate the 3D image in the direction indicated by the arrow to ultimately align the axial plane indicator 16 and the sagittal plane indicator 18 such that they intersect perpendicularly, as shown in FIG. 37. FIG. 37 shows the projection of the C-arm angulation across the mitral valve horizontal plane for proposed transapical access. A multi-image (e.g., 20-image) snapshot view may be created that shows the movement of the 3D inverted MIP image 90 degrees superiorly, then inferiorly, then to the right anterior oblique (RAO) position. This reduces the amount of iodinated contrast that needs to be administered and reduces the amount of radiation applied to the patient, while giving physicians more insight on what to anticipate during the procedure. This technique can be applied to other anatomical structures for adequate localization in any fluoroscopic suite utilizing C-arm angulation and projection of images onto a visual display.

With reference to the tricuspid inferior vena cava valve (or CAVI) example provided above, a similar volume rendered MIP may be developed. The MIP inversion and 3D volume image can include segmentation of the ribs, spine, right atrium, right ventricle, inferior vena cava, and the first hepatic vein which may be projected in a black and white radiograph simulation. Original snapshots may be restored one at a time of the right atrium-inferior vena cava plane, and the inferior cava-hepatic vane plane separately into the 3D inverted volume MIP. It may be desirable to mark the corresponding spinous processes in the coronal and sagittal views in each respective plane. C-arm angles may be obtained by aligning the axial and sagittal planes in the 3D window such that they interest perpendicularly. A multi-image (e.g., 20-image) snapshot video may be made to show the movement of 3D inverted MIP 90 degrees superiorly, then inferiorly, then to the RAO position from this baseline angulation. During an inferior vena cava procedure, 2D and 3D tranesophageal echocardiography (TEE) may be used to survey the right atrium for any clots or pericardial effusion, intraprocedure stent or device migration, observance of pre- and post-procedure coronary sinus flow, and the presence or absence of a paravalvular leak. A new pericardial effusion could suggest concern for iatrogenic perforation of the right atrium, and if such an effusion is present, cine loops can be made of the right atrium-inferior vena cava junction in an oblique and axial cross-sectional view which could indicate a leak in the absence of contrast extravasation to adjacent structures. Non-traditional views may provide preferable angles for TEE in TIVI cases. To visualize the right atrium-inferior vena cava junction, it is possible to start in a 4 chamber view and advance to the level of the coronary sinus. Then, the probe angulation may be increased to bring the mouth of the inferior vena cava into the plane. Other parameters that may be evaluated include the right ventricle size, the right ventricle fractional area change (FAC), gradients across the implanted device, pulmonary artery systolic pressure, and the tricuspid annular plane systolic excursion (TAPSE). Pulsed wave Doppler may be run across the right atrium-inferior vena cava junction to follow peak and/or mean gradients across the implanted valve. The hepatic vein and pulmonary vein Doppler flow patterns may also be evaluated. After the procedure, gated computer tomography angiography (CTA) or clinical target volume (CTV) of the abdomen may be performed to evaluate function and positioning of the implanted valve. A two-phase gated CTA and CTV may be initially performed, although a CTV may not be necessary, as the gated CTA abdomen images in and of themselves could be adequate for evaluation of regurgitant flow and valve function. Cine loops through the axial and sagittal slices of the inferior vena cava demonstrates opening and closure of the implanted valve device by the dynamic change in hounsfield units across the valve and a demonstrable lack of flow into the distal inferior vena cava with valve leaflet closure, and flow with leaflet opening.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. For example, the specific combination and order of steps presented is just one possibility, as the present method may include a combination of steps that has fewer, greater, or different steps than that shown here. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A method of analyzing a hollow anatomical structure of interest in a patient's body for percutaneous implantation, comprising the steps of:
  acquiring image data relating to an anatomical region of interest that at least partially includes the anatomical structure of interest;
  generating a segmented model of the anatomical region of interest using the acquired image data, wherein the segmented model comprises a first model;
  obtaining one or more images of the anatomical structure of interest by sectioning out intervening anatomical structures from the first model, wherein sectioning out intervening anatomical structures comprises removing from the first model one or more portions thereof containing the intervening anatomical structures;
  identifying one or more pertinent landmarks of the anatomical structure of interest in the one or more obtained images;
  measuring at least one of a circumference, a maximal diameter, or a minimal diameter of one or more features of the anatomical structure of interest contained in the one or more obtained images to determine an anatomical structure size;
  reconciling the anatomical structure size and an implant size;

identifying a point of access into the patient's body for percutaneous implantation of the implant;

displaying a visual representation of the identified point of access on a model of the patient's body that includes a representation of the outer surface of the patient's body, wherein the model of the patient's body comprises a second model; and removing from the second model, one or more layers of the second model each corresponding to a respective anatomical structure disposed between the outer surface of the patient's body and the anatomical structure of interest, and following the removal of each of the one or more layers, determining whether the identified point of access intersects one or more anatomical structures disposed between the outer surface of the patient's body and the anatomical structure of interest based on the displayed visual representation of the identified point of access, wherein the visual representation of the identified point of access remains displayed on the second model as each of the one or more layers of the second model is removed from the second model.

2. The method of claim 1, wherein the acquired image data comprises computed tomography (CT) data and the first model comprises a segmented CT model.

3. The method of claim 1, further comprising determining a trajectory angle at the point of access.

4. The method of claim 3, wherein the visual representation of the identified point of access is oriented at the determined trajectory angle.

5. The method of claim 1, further including the step of estimating an anatomical structure volume.

6. The method of claim 1, wherein the anatomical structure of interest is a mitral valve.

7. The method of claim 6, wherein the one or more pertinent landmarks comprise one or more of: a mitral valve leaflet tip and an intersection point of the mitral valve leaflets and the annulus of the mitral valve.

8. The method of claim 1, wherein the anatomical structure of interest is a left atrial appendage.

9. The method of claim 8, wherein the one or more landmarks comprise one or more of: a pulmonary vein; a location of the Coumadin ridge; the transverse pericardial sinus; the circumflex artery; the mitral valve; the left atrium, the interatrial septum, and the superior vena cava and inferior vena cava transition into the interatrial septum.

10. The method of claim 1, wherein the anatomical structure of interest is a tricuspid inferior vena cava valve.

11. The method of claim 10, wherein the one or more landmarks comprise one or more of: the right atrium-inferior vena cava plane, the inferior vena cava ostium, and the first hepatic vein.

12. The method of claim 1, further including creating a computer aided design (CAD) model of at least a portion of the anatomical structure of interest, and the reconciling step comprises importing a model of the implant into the CAD model.

13. The method of claim 1, further including acquiring a printed model of at least a portion of the anatomical structure of interest, and the reconciling step comprises inserting a physical model of the implant into the printed model.

14. The method of claim 1, wherein removing one or more layers from the second model comprises removing the one or more layers layer-by-layer.

15. A method of analyzing a hollow anatomical structure of interest in a patient's body for percutaneous implantation, comprising the steps of:

acquiring a model of an anatomical region of interest that at least partially includes the anatomical structure of interest, wherein the model of the anatomical region of interest is a first model and is generated from image data relating to the anatomical region of interest;

obtaining one or more images of the anatomical structure of interest by sectioning out intervening anatomical structures from the first model, wherein sectioning out intervening anatomical structures comprises removing from the first model one or more portions thereof containing the intervening anatomical structures;

acquiring data relating to the anatomical structure of interest from the one or more images of the anatomical structure of interest;

determining a size of an implant to be implanted into the anatomical structure of interest based on the acquired data;

identifying a point of access into the patient's body for percutaneous implantation of the implant;

displaying a visual representation of the identified point of access on a model of the patient's body that includes a representation of the outer surface of the patient's body, wherein the model of the patient's body is a second model; and removing from the second model, one or more layers of the second model each corresponding to a respective anatomical structure disposed between the outer surface of the patient's body and the anatomical structure of interest, and following the removal of each of the one or more layers, determining whether the identified point of access intersects one or more anatomical structures disposed between the outer surface of the patient's body and the anatomical structure of interest based on the displayed visual representation of the identified point of access, wherein the visual representation of the identified point of access remains displayed on the second model as each of the one or more layers of the second model is removed from the second model.

16. The method of claim 15, wherein the step of acquiring data relating to the anatomical structure of interest comprises acquiring one or more measurements relating to one or more features of the anatomical structure of interest, and the step of determining the size of the implant comprises determining the size of the implant based on the acquired measurement(s).

17. The method of claim 15, wherein the step of acquiring data relating to the anatomical structure of interest comprises acquiring data relating to a blood volume of the anatomical structure of interest.

18. The method of claim 17, further comprising generating a model of the anatomical structure of interest based on the blood volume data, wherein the model of the anatomical structure of interest is a third model, and further wherein the step of determining the size of the implant comprises determining the size of the implant using the model generated from the blood volume data.

19. The method of claim 18, wherein the third model comprises a model of the interior surface of the anatomical structure of interest.

20. The method of claim 15, wherein removing one or more layers from the second model comprises removing the one or more layers layer-by-layer.

21. A non-transitory, computer-readable storage medium storing instructions thereon that when executed by one or more electronic processors causes the one or more processors to carry out the method of:

acquiring a model of an anatomical region of interest in a patient's body that includes the anatomical structure of interest, wherein the model of the anatomical region of interest is a first model and is generated from image data relating to the anatomical region of interest;

obtaining one or more images of the anatomical structure of interest by sectioning out intervening anatomical structures from the first model, wherein sectioning out intervening anatomical structures comprises removing from the first model one or more portions thereof containing the intervening anatomical structures;

acquiring data relating to the anatomical structure of interest;

determining a size of an implant to be implanted into the anatomical structure of interest based on the acquired data;

identifying a point of access into the patient's body for percutaneous implantation of the implant;

displaying a visual representation of the identified point of access on a model of the patient's body that includes a representation of the outer surface of the patient's body, wherein the model of the patient's body is a second model; and removing from the second model, one or more layers of the second model each corresponding to a respective anatomical structure disposed between the outer surface of the patient's body and the anatomical structure of interest, and following the removal of each of the one or more layers, determining whether the identified point of access intersects one or more anatomical structures disposed between the outer surface of the patient's body and the anatomical structure of interest based on the displayed visual representation of the identified point of access, wherein the visual representation of the identified point of access remains displayed on the second model as each of the one or more layers of the second model is removed from the second model.

* * * * *